US011504259B2

(12) United States Patent
DiAngelo et al.

(10) Patent No.: US 11,504,259 B2
(45) Date of Patent: Nov. 22, 2022

(54) CONTROLLED TENSION DEVICE FASTENING DEVICES, SYSTEMS, AND METHODS

(71) Applicant: University of Tennessee Research Foundation, Knoxville, TN (US)

(72) Inventors: Denis J. DiAngelo, Germantown, TN (US); Cody Bateman, Bartlett, TN (US); Chloe Chung, Lakeland, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 431 days.

(21) Appl. No.: 16/464,833

(22) PCT Filed: Dec. 5, 2017

(86) PCT No.: PCT/US2017/064696
§ 371 (c)(1),
(2) Date: May 29, 2019

(87) PCT Pub. No.: WO2018/106679
PCT Pub. Date: Jun. 14, 2018

(65) Prior Publication Data
US 2019/0314186 A1    Oct. 17, 2019

Related U.S. Application Data

(60) Provisional application No. 62/429,940, filed on Dec. 5, 2016.

(51) Int. Cl.
*A61F 5/02* (2006.01)
*A61F 5/01* (2006.01)

(52) U.S. Cl.
CPC .............. *A61F 5/022* (2013.01); *A61F 5/024* (2013.01); *A61F 2005/0197* (2013.01)

(58) Field of Classification Search
CPC .......... A61H 1/0292; A61H 2201/1607; A61H 2201/1621; A61H 2201/163;
(Continued)

(56) References Cited

U.S. PATENT DOCUMENTS 3,156,430 A * 11/1964 Zivi .......................... A61F 5/04
242/376
3,889,664 A    6/1975 Heuser et al.
(Continued)

FOREIGN PATENT DOCUMENTS

WO    WO 2006/090380 A2    8/2006
WO    WO 2018/187566 A1    10/2018

OTHER PUBLICATIONS

International Search Report corresponding to International Patent Application No. PCT/US2018/026248 dated Jun. 19, 2018.
(Continued)

*Primary Examiner* — Ophelia A Hawthorne
(74) *Attorney, Agent, or Firm* — Jenkins, Wilson, Taylor & Hunt, P.A.

(57) ABSTRACT

Devices, systems, and methods for maintain a preselected tension between a first portion and a second portion of an orthotic brace include a controlled tension unit that includes a housing coupled to a first portion of the orthotic brace, the housing having a cavity formed therein, one or more constant-force spring mounted at or near a first end of the cavity, and a connector cable having a first end connected to an end of the one or more constant-force spring and a second end extending out of the housing through a second end of the cavity. The second end of the connector cable is configured to connect with a coupling element coupled to a second portion of the orthotic brace. In this arrangement, the
(Continued)

controlled tension unit is configured to maintain a preselected tension between the first portion and the second portion of the orthotic brace.

25 Claims, 22 Drawing Sheets

(58) Field of Classification Search
CPC .... A61H 2201/1642; A61H 2201/1652; A61H 1/0266; A61H 2201/1676; A61H 2205/081; A61H 1/0244; A61H 2201/1628; A61H 2203/0487; A61H 1/02; A61H 1/0237; A61H 2201/164; A61H 2205/088; A61H 3/008; A63B 21/0552; A63B 21/0557; A63B 21/4009; A63B 21/4011; A63B 21/4015; A63B 21/00043; A63B 21/02; A63B 23/0405; A63B 21/4039; A63B 2023/006; A63B 21/0023; A63B 2220/51; A63B 23/04; A63B 69/0059; A63B 21/068; A63B 2208/0204; A63B 21/065; A63B 23/035; A63B 2023/003
See application file for complete search history.

(56) References Cited

U.S. PATENT DOCUMENTS

| | | | |
|---|---|---|---|
| 4,202,327 A * | 5/1980 | Glancy | A61F 5/022 602/19 |
| 4,483,330 A | 11/1984 | Jacobsen et al. | |
| 4,688,559 A | 8/1987 | Vito et al. | |
| 4,790,301 A | 12/1988 | Silfverskiold | |
| 5,462,518 A | 10/1995 | Hatley et al. | |
| 5,472,410 A | 12/1995 | Hamersly | |
| 6,776,767 B2 | 8/2004 | Reinecke et al. | |
| 7,070,572 B2 | 7/2006 | Reinecke et al. | |
| 7,445,608 B2 | 11/2008 | Dunfee et al. | |
| 7,591,797 B2 | 9/2009 | Hakonson et al. | |
| 8,012,113 B2 | 9/2011 | Lee et al. | |
| 8,657,769 B2 | 2/2014 | Ingimundarson et al. | |
| 8,845,566 B2 | 9/2014 | Johnson et al. | |
| 9,480,593 B2 | 11/2016 | DiAngelo et al. | |
| 11,213,419 B2 | 1/2022 | DiAngelo et al. | |
| 2004/0073150 A1 | 4/2004 | Roballey | |
| 2005/0010150 A1 | 1/2005 | Firsov | |
| 2006/0079821 A1* | 4/2006 | Rauch | A61F 5/022 602/19 |
| 2012/0253251 A1 | 10/2012 | Thornton et al. | |
| 2014/0276308 A1* | 9/2014 | DiAngelo | A61F 5/03 602/19 |
| 2015/0231017 A1 | 8/2015 | Kazemi Banyhashemi et al. | |
| 2016/0296361 A1 | 10/2016 | Leake et al. | |
| 2020/0375778 A1 | 12/2020 | DiAngelo et al. | |

OTHER PUBLICATIONS

IPRP and Written Opinion corresponding to International Patent Application No. PCT/US2018/026248 dated Oct. 8, 2019.
Notice of Allowance corresponding to U.S. Appl. No. 16/497,322 dated Feb. 8, 2021.
Disc Disease Solutions (DDS) 500 Lumbar Decompression Brace with Panels, http://discdiseasesolutions.com/products/dds-500-back-brace/, webpage, accessed May 10, 2021.
Akay et al., "Ant Colony Optimization Approach for Classification of Occupational Low Back Disorder Risks," Hum Factors Ergon Manuf, vol. 19, pp. 1-14 (2009).
Apfel, "Restoration of disk height through non-surgical spinal decompression is associated with decreased discogenic low back pain: a retrospective cohort study," BMC Muscluoskelet Disord, vol. 11, pp. 1-6 (2010).
Baena-Beato, "Effects of Different Frequencies (2-3 Days/Week) of Aquatic Therapy Program in Adults with Chronic Low Back Pain. A Non-Randomized Comparison Trial," Pain Med, vol. 14, pp. 145-158, 2013.
Bigos et al., "Acute low back problems in adults. Clinical practice guidelines No. 14," P. H. S. US Department of Health and Human Services, Agency for Health Care Policy and Research, Ed., ed, 167 pages (1994).
Brecher, "Editor's Message," JAOA, vol. 101, No. 4, 2 pages (2001).
Brown et al., "Sensory and sympathetic innervation of the vertebral endplate in patients with degenerative disc disease," J Bone Joint Surg, vol. 79-B, No. 1, pp. 147-153 (1997).
Childs et al., "Responsiveness of the Numeric Pain Rating Scale in Patient with Low Back Pain," Spine, vol. 30, No. 11, pp. 1331-1334 (2005).
Chou, "Low back pain (chronic)," BMJ Clinical Evidence, vol. 10, pp. 1-41 (2010).
DiAngelo et al., "A novel distractive and mobility-enabling lumbar spinal orthosis," Journal of Rehabilitation and Assistive Technologies Engineering, vol. 3, pp. 1-10 (2016).
DiAngelo et al., "Robotized Method for Comparative Testing of Back Support Devices," Journal of Mississippi Academy of Sciences, pp. 179-186 (2015a).
DiAngelo et al., "Towards the Design of a Distractive and Mobility-Enabling Back Support Device," Journal of Mississippi Academy of Sciences, pp. 193-200 (2015b).
Dundar et al., "Clinical Effectiveness of Aquatic Exercise to Treat Chronic Low Back Pain: A Randomized Controlled Trial," Spine, vol. 34, No. 14, pp. 1436-1440 (2009).
Ferrara et al., "A biomechanical assessment of disc pressures in the lumbosacral spine in response to external unloading forces," Spine J, vol. 5, pp. 548-553, 2005.
Fritzell et al., "2001 Volvo Award Winner in Clinical Studies: Lumbar Fusion Versus Nonsurgical Treatment for Chronic Low Back Pain: A Multicenter Randomized Controlled Trial from the Swedish Lumbar Spine Study Group," Spine, vol. 26, No. 23, pp. 2521-2534 (2001).
Hagg et al., "The clinical importance of changes in outcome scores after treatment for chronic low back pain," Eur Spine J, vol. 12, pp. 12-20 (2003).
Hoy et al., "The global burden of low back pain: estimates from the Global Burden of Disease 2010 Study," Ann Rheum Dis, vol. 73, pp. 968-974 (2014).
Jensen, "Biomechanics of the lumbar intervertebral disk: a review," Phys Ther, vol. 60, No. 6, pp. 765-773 (1980).
Johnson et al., "Active Spinal Orthosis to Reduce Lumbar Postural Muscle Activity in Flexed Postures," JPO, vol. 28, No. 3, pp. 109-113 (2016).
Kawchuk et al., "A non-randomized clinical trial to assess the impact of nonrigid, inelastic corsets on spine function in low back pain participants and asymptomatic controls," Spine J, vol. 15, pp. 2222-2227 (2015).
Koes et al., "Diagnosis and treatment of low back pain," BMJ, vol. 332, pp. 1430-1434 (2006).
Leake. The VerteCore Lift, vertecorelift. Available: https://vertecorelift.wordpress.com/how-vertecore-lift-works/; accessed May 11, 2021.
Mirovsky et al., "The effect of ambulatory lumbar traction combined with treadmill on patients with chronic low back pain," J Back Musculoskelet Rehabil, vol. 19, pp. 73-78 (2006).
Pensri et al., "Biopsychological Factors and Perceived Disability in Saleswomen with Concurrent Low Back Pain," Saf Health Work, vol. 1, pp. 149-157 (2010).
Simmons, "Development of a Mobility-Enabling Spinal Orthosis and Methods for Evaluating and Developing Spinal Orthoses on a Robotic Platform," PhD, UTHSC Orthopedic Surgery & Biomedical Engineering, The University of Tennessee Health Science Center, 93 pages (2014).
Stubbs, "Use of a Multi-Axis Robotic Testing Platform to Investigate the Sagittal Mechanics of the Multi-Body Lumbar Spine," Master of Science, Department of Orthopaedic Surgery and Biomedical Engineering, The University of Tennessee Health Science Center, 54 pages (2014).

(56) References Cited

OTHER PUBLICATIONS

Tosteson et al., "The Cost Effectiveness of Surgical versus Non-Operative Treatment for Lumbar Disc Herniation over Two Years: Evidence from the Spine Patient Outcomes Research Trial (SPORT)," Author manuscript, pp. 1-19, published in final edited form as: Spine, vol. 33, pp. 2108-2115 (2008).

International Search Report and Written Opinion corresponding to International Patent Application No. PCT/US2017/064696 dated Feb. 22, 2018.

International Preliminary Report on Patentability (Chapter 1 of the Patent Cooperation Treaty) corresponding to International Patent Application No. PCT/US2017/064696 dated Jun. 20, 2019.

Wong et al., "Biomechanical evaluation of the Milwaukee brace," Prosthet Orthot Int., vol. 22, No. 1, pp. 54-67 (1998).

Zeh et al., "The flexible Triac™-Brace for conservative treatment of idiopathic scoliosis. An alternative treatment option?" Acta Orthop Belg., vol. 74, No. 4, pp. 512-521 (2008).

Bernard et al. "The carbon brace," Scoliosis, vol. 8, No. 3, pp. 1-19 (2013).

Notification Concerning Availability of the Publication of the International Application corresponding to International Application No. PCT/US2017/064696 dated Jun. 14, 2018.

Andersson, "Epidemiologic features of chronic low-back pain," The Lancet, vol. 354, pp. 581-585 (1999).

Aubin et al. "Variability of Strap Tension in Brace Treatment for Adolescent Idiopathic Scoliosis," Spine, vol. 24, No. 4, pp. 349-354 (1999).

Bateman, "Design, Validation, and Clinical Testing of a Novel Fastening Device for a Scoliosis Brace," Master's Thesis, UTHSC ET/D Library, pp. 1-67 (2017).

Bible et al., "Normal functional range of motion of the lumbar spine during 15 activities of daily living," J Spinal Disord Tech, vol. 23, No. 2, pp. 106-112 (2010).

Brox, "Randomized clinical trial of lumbar instrumented fusion and cognitive intervention and exercises in patients with chronic low back pain and disc degeneration," Spine, vol. 28, No. 17, pp. 1913-1921 (2003).

Cannon et al., "Evidence on the Ability of a Pneumatic Decompression Belt to Restore Spinal Height Following an Acute Bout of Exercise," JMPT, vol. 39, No. 4, pp. 304-310 (2016).

Chung et al. "A mechanical analog thoracolumbar spine model for the evaluation of scoliosis bracing technology," Journal of Rehabilitation and Assistive Technologies Engineering, vol. 5, pp. 1-9 (2018).

Chung, "Scoliosis Analog Model for the Evaluation of Bracing Technology," Theses and Dissertations (ETD), Paper 445, pp. 1-94 (2015).

Crisco, "Optimal marker placement for calculating the instantaneous center of rotation," J Biomech, vol. 27, No. 9, pp. 1183-1187 (1994).

Cuesta-Vargas et al., "Deep water running and general practice in primary care for non-specific low back pain versus general practice alone: randomized controlled trial," Clin Rheumatol, vol. 31, pp. 1073-1078 (2012).

Deyo, "Low back pain," N Engl J Med, vol. 344, No. 5, pp. 363-370 (2001).

ExMS-1, the Electromechanically-Activated Spinal Brace (Exo Dynamics, LLC, MI, USA), 10 pages, product page dated 2020, retrieved online Jun. 17, 2021.

Fritz, "Physical therapy for acute low back pain: associations with subsequent healthcare costs," Spine, vol. 33, No. 16, pp. 1800-1805 (2008).

Gilad, "A study of vertebra and disc geometric relations of the human cervical and lumbar spine," Spine, vol. 11, No. 2, pp. 154-157 (1986).

Katz et al. "Brace wear control of curve progression in adolescent idiopathic scoliosis," The Journal of Bone & Joint Surgery, vol. 92(6), pp. 1343-1352 (2010).

Kelly, "A Multiaxis Programmable Robot for the Study of Multibody Spine Biomechanics Using a Real-Time Trajectory Path Modification Force and Displacement Control Strategy," J Med Devices, vol. 7, pp. 1-7(2013).

Krag et al., "Comparison of three lumbar orthoses using motion assessment during task performance," Spine, vol. 28, No. 20, pp. 2359-2367 (2003).

Lantz et al., "Lumbar spine orthosis wearing: I. Restriction of gross body motions," Spine, vol. 11, No. 8, pp. 834-837 (1986).

Lou et al. "An objective measurement of brace usage for the treatment of adolescent idiopathic scoliosis," Med Eng Phys., 33(3), pp. 290-294 (2011).

Loukos et al., "Analysis of the corrective forces exerted by a dynamic derotation brace (DDB)," Prosthet Orthot Int., vol. 35(4), pp. 365-372 (2011).

Medical Coverage Policy, "Thoracic Lumbosacral Orthosis with Pneumatics," Blue Cross Blue Shield, 2 pages (2013).

Modic et al., "Lumbar Degenerative Disk Disease," Radiology, vol. 245, No. 1, pp. 43-61 (2007).

Notice of Allowance corresponding to U.S. Appl. No. 16/497,322 dated Sep. 2, 2021.

Corrected Notice of Allowability corresponding to U.S. Appl. No. 16/497,322 dated Sep. 16, 2021.

Osprey Isoform Hipbelt (Osprey Packs, Inc., Cortez, CO, USA), 6 pages, retrieved online Jun. 17, 2021.

Pham et al. "Study of the pressures applied by a Cheneau brace for correction of adolescent idiopathic scoliosis," Prosthet Orthot Int., vol. 32(3), pp. 345-355 (2008).

S.P.I.N.E. Brace (Cybertech Medical/ottobock), instruction manual, 8 pages (2018).

The Aspen LSO (Aspen Medical Products, CA, USA), brochure, 2 pages (2019).

The Cybertech Orthosis (Biocybernetics International, CA, USA), product webpage, 3 pages, retrieved online Jun. 17, 2021.

The Orthotrac Pneumatic Vest (Orthofix, Inc., TX, USA), instruction manual, 6 pages (2003).

The QuikDraw Brace (Aspen Medical Products, CA, USA), brochure, 2 pages (2019).

The Vertetrac Ambulatory Traction System (Meditrac Ltd, TX, USA), brochure, 2 pages, n/d.

Wong et al. "The effect of rigid versus flexible spinal orthosis on the clinical efficacy and acceptance of the patients with adolescent idiopathic scoliosis," Spine, 33(12), pp. 1360-1365 (2008a).

Wong et al. "The effect of rigid versus flexible spinal orthosis on the gait pattern of patients with adolescent idiopathic scoliosis," Gait & Posture, vol. 27, pp. 189-195 (2008b).

\* cited by examiner

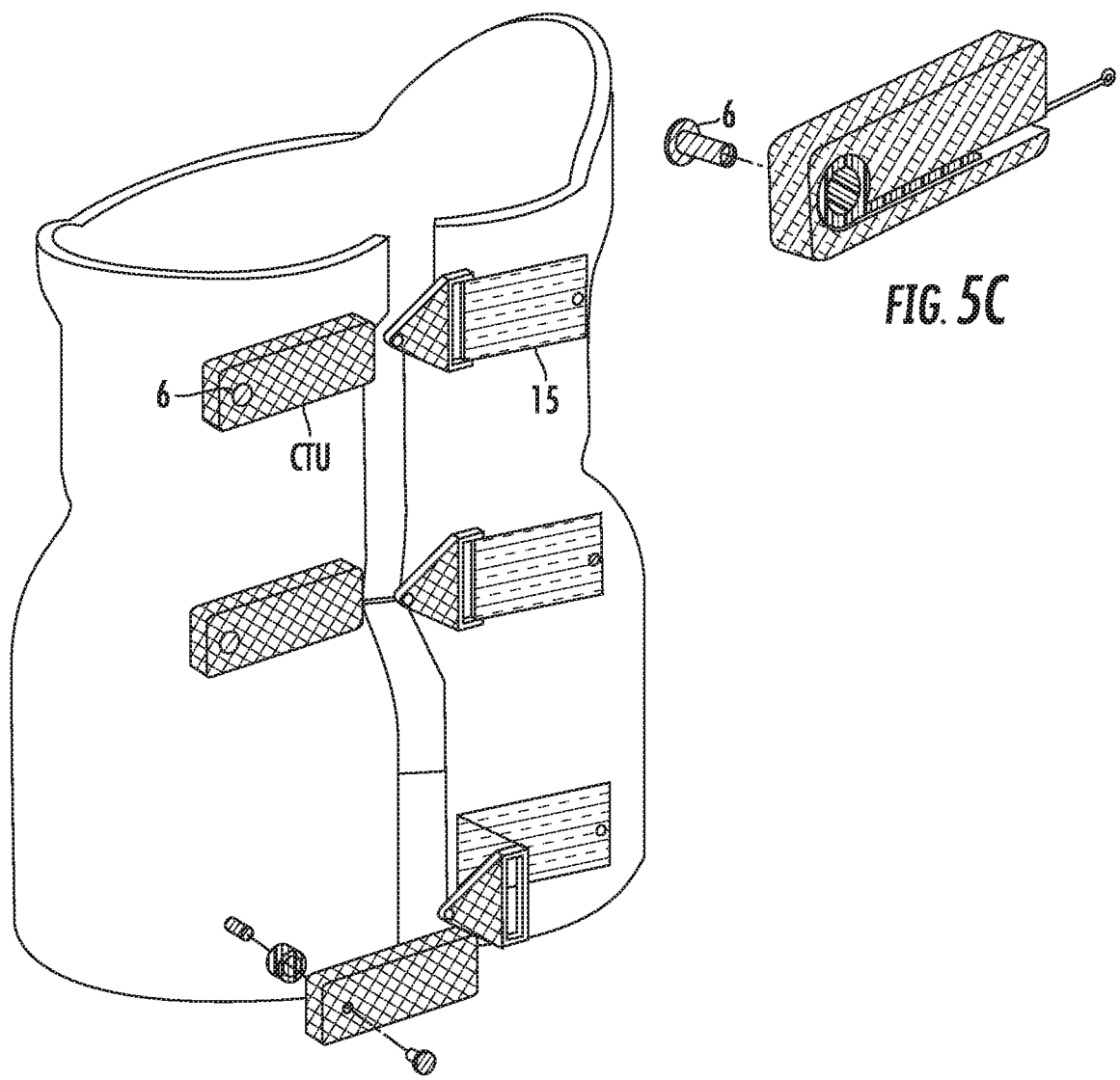

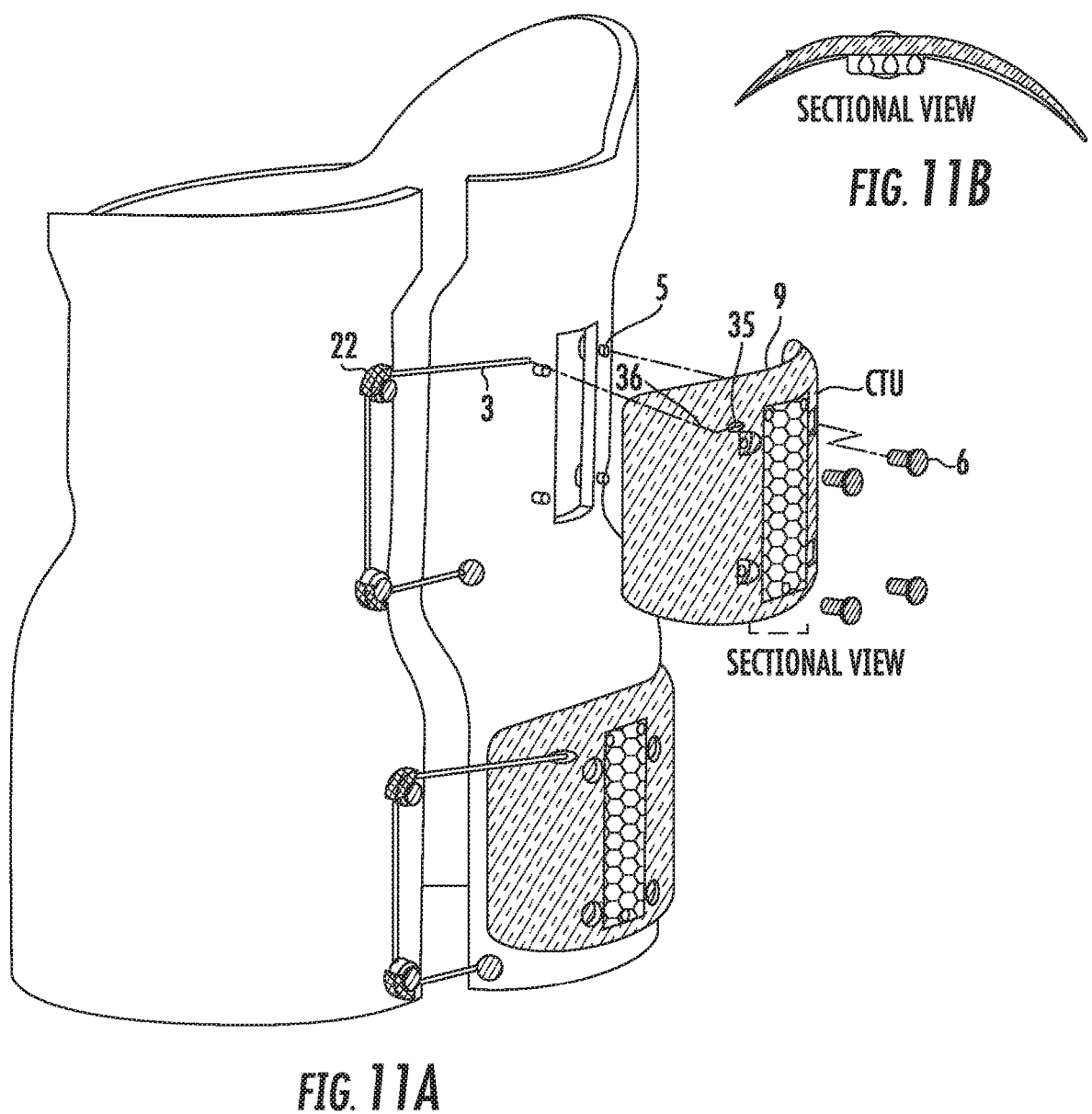

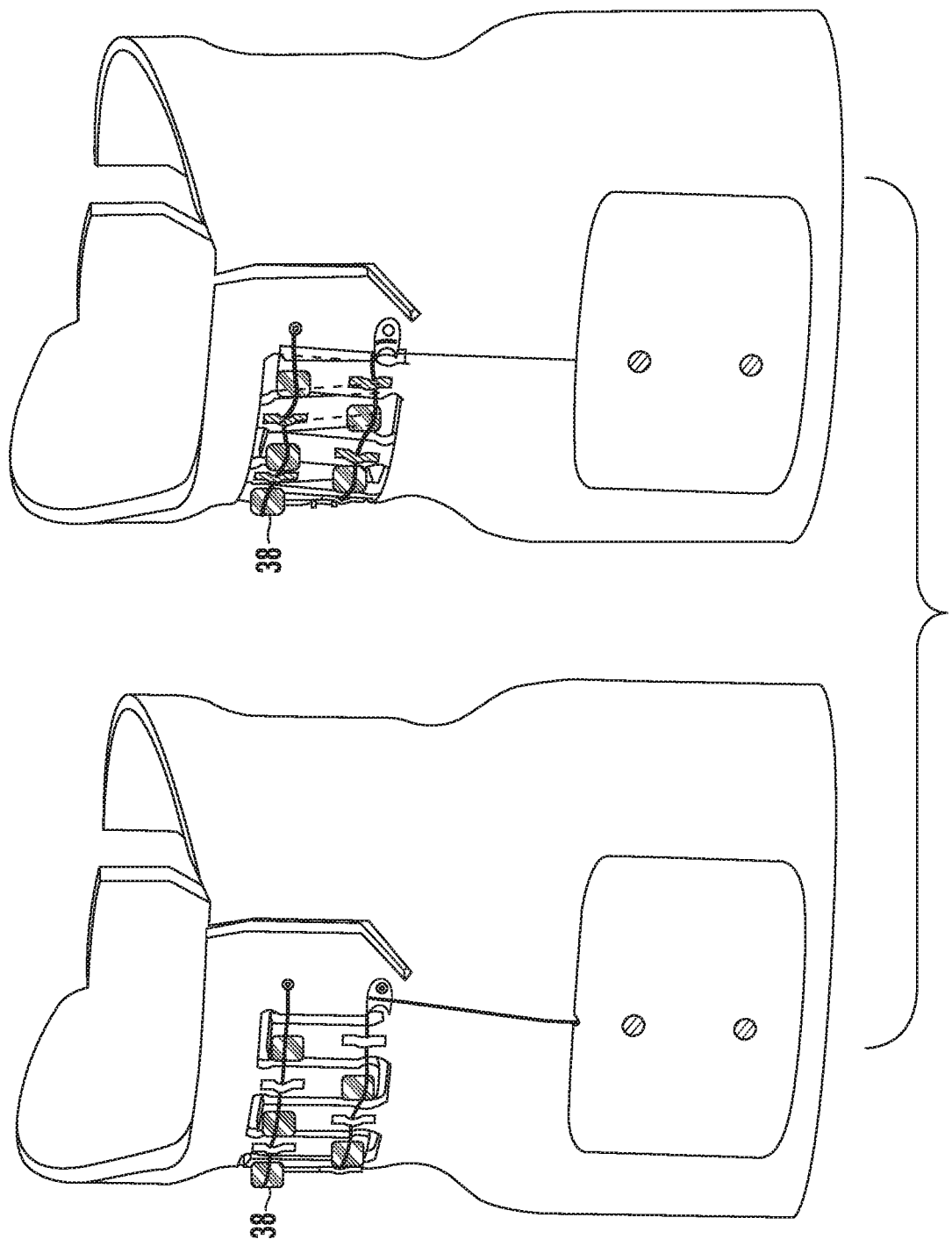

CONTROLLED TENSION DEVICE FASTENING DEVICES, SYSTEMS, AND METHODS

CROSS-REFERENCE TO RELATED APPLICATIONS

This application is a 35 U.S.C. Section 371 national phase application of PCT International Application Serial No. PCT/US17/064696, filed Dec. 5, 2017, which claims benefit of U.S. Provisional Patent Application Ser. No. 62/429,940, filed Dec. 5, 2016, herein incorporated by reference in its entirety.

TECHNICAL FIELD

The subject matter disclosed herein relates generally to fastening devices. More particularly, the subject matter disclosed herein relates to fastening devices that provide tension for orthotic braces.

BACKGROUND

Braces are used as conservative treatment for adolescent idiopathic scoliosis and primarily include a rigid, flexible or composite outer shell. Each brace is commonly custom fabricated to better fit around the patient's upper torso and pelvic anatomy. Fastening devices, like Velcro straps, are used to engage and secure the brace around the upper body and apply corrective forces to the spine. However, Velcro strapping systems have been associated with strap loosening and tension loss following two or more weeks of daily brace wear [1], after various daily living activities [2,3], and/or when lying down [1-5].

Current biomechanical research has determined that the majority of the brace's corrective force capacity comes from the fastening devices and not the native brace shell itself [6]. The force-displacement or stiffness properties of a scoliosis brace without any strap tension is negligible compared to the force-displacement or stiffness properties of the brace with the fastening devices engaged. Thus, loss of strap tension decreases the brace stiffness properties and reduces the corrective spinal force applied by the brace, both contributing to a loss of spinal correction that negates the benefit of wearing the brace.

In addition, besides reduced corrective forces and spinal correctional losses, braces have also been reported as being uncomfortable to wear, resulting in reduced brace wear time or complete abandonment [8]. To address user compliancy problems, monitoring systems have been employed to determine whether the user wears the brace over the prescribed time [7]. In most cases, braces are to be worn 18 to 21 hours per day. More recently feedback systems have been proposed for measuring and/or monitoring compliance and/or quality of brace usage [1,7]. These devices are largely warning systems and have not yet provided active adjustment to correct the strap tension loss but rather rely on the caregiver or practitioner to manually readjust the strap tension settings. More flexible braces have also been designed to address the user compliancy problems of discomfort associated with wearing a rigid brace. However, any additional comfort provided by a more flexible brace occurs at the expense of lesser brace corrective force capacity, i.e., minimizing the primary role of the brace [8,9].

Regardless of compliance monitors, strap tension is reset manually by the user or a caregiver and may frequently be set below the original prescribed value of the practitioner because this is more comfortable to the brace wearer. In any case, the ongoing loosening of the Velcro straps perpetuates the need for the strap monitoring/adjustment cycle.

SUMMARY

In accordance with this disclosure, devices, systems, and methods for maintaining a preselected tension between a first portion and a second portion of an orthotic brace are provided. In one aspect, a controlled tension unit for an orthotic brace is provided. The controlled tension unit includes a housing, one or more constant-force spring mounted at or near a first end of the housing, and a connector cable having a first end connected to an end of the one or more constant-force spring and a second end extending out of the housing (e.g., at a second end of the housing).

In another aspect, an orthotic brace is provided. The orthotic brace includes a controlled tension unit coupled to a first portion of the orthotic brace, the controlled tension unit comprising one or more constant-force spring and a connector cable having a first end connected to an end of the one or more constant-force spring and a second end extending therefrom. A coupling element is coupled to a second portion of the orthotic brace, the coupling element being configured to couple with the second end of the connector cable, the second portion being separated from the first portion by a gap. In this arrangement, the controlled tension unit is configured to maintain a preselected tension between the first portion and the second portion of the orthotic brace.

In yet another aspect, a method for maintaining a preselected tension between a first portion and a second portion of an orthotic brace is provided. The method includes connecting a controlled tension unit to the first portion of the orthotic brace, the controlled tension unit comprising one or more constant-force spring and a connector cable having a first end connected to an end of the one or more constant-force spring and a second end extending therefrom. The method further includes connecting a coupling element to the second portion of the orthotic brace, and coupling the coupling element with the second end of the connector cable.

In another aspect, a method for dynamizing a standard scoliosis brace is provided. The method includes the addition of various cut-out features combined with the CTU devices and one or more riser components. The features can include a cut-out cantilever flap located around the epical pad, finger like cut-out sections, or interweaving tabs. The riser converts the controlled tension along the cable to a directional force perpendicular to the cable direction and displace the cut-out features inward.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 5B is a perspective view of a scoliosis brace incorporating an alternative configuration of attaching controlled tension devices to the brace according to an embodiment of the presently disclosed subject matter;

FIG. 5C is a view of the backside of a CTU for use in the scoliosis brace shown in FIG. 5B;

FIGS. 11A and 11B are perspective and sectional views of a scoliosis brace incorporating controlled tension devices according to an embodiment of the presently disclosed subject matter;

FIG. 12E and FIG. 12F are perspective views a dynamized scoliosis brace with interweaving tabs located at the anterolateral side of the brace with a riser located above the tabs. A pulley or system of pulleys is used to direct a cable over one or more risers that connect to a controlled tension device. Cable tension acts to displace the tabs inward normal to the brace surface.

DETAILED DESCRIPTION

The presently disclosed subject matter relates to an alternative fastening device, or controlled tension unit (CTU), for a scoliosis brace, which in some embodiments allows the user to (1) set the strap tension to the prescribed value as determined by the orthotist at the time of brace fitting; (2) maintain the prescribed strap tension during a variety of typical daily living activities to ensure the corrective force capacity of the scoliosis brace was present and the occurrence of strap loosening and tension loss was minimized; and/or (3) make the brace more compliant and without compromising the corrective force capacity of the brace.

Figure 1A:
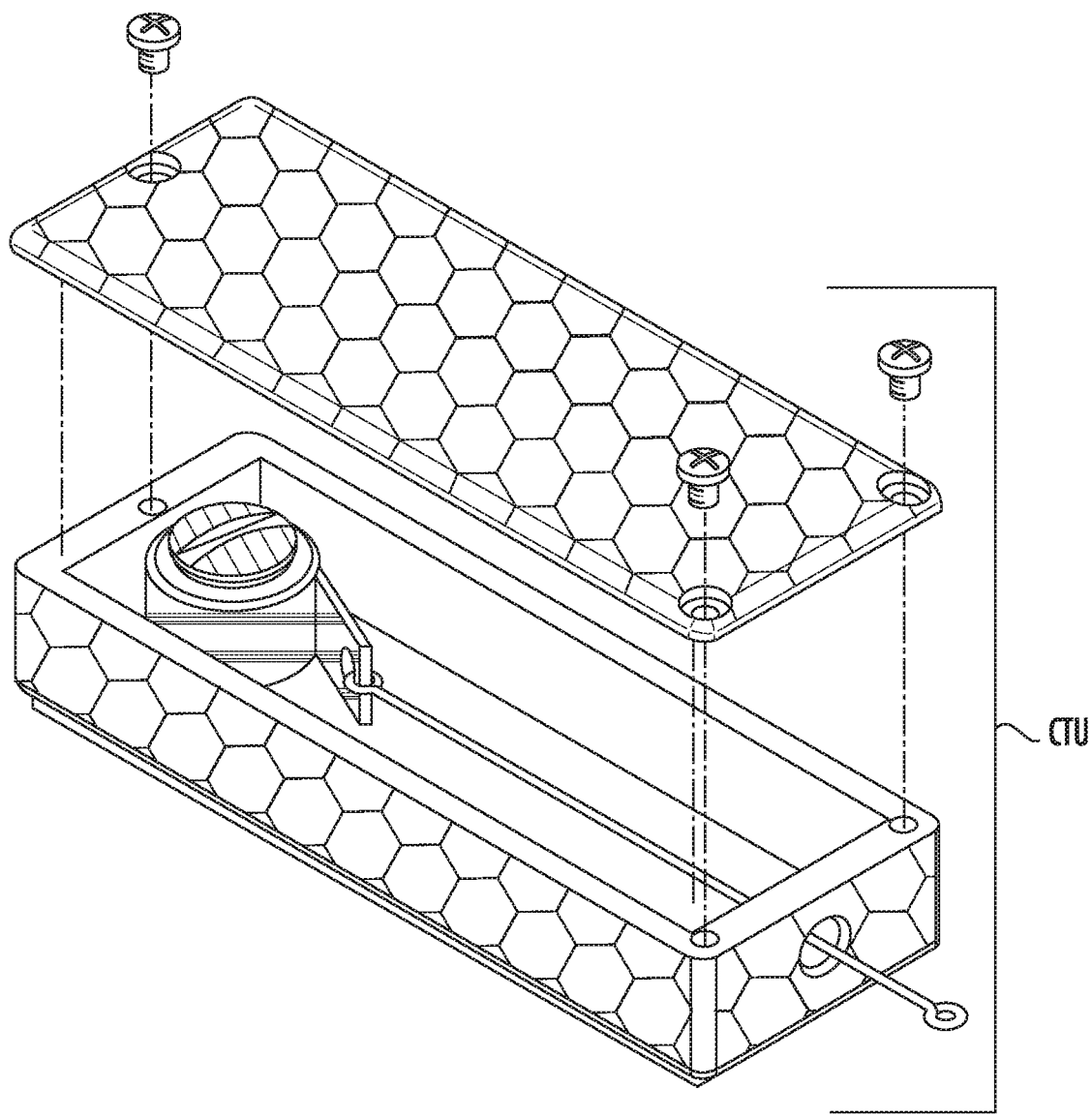
FIG. 1A is a perspective view of a controlled tension device in which the spring is held inside a housing having a cavity formed therein according to an embodiment of the presently disclosed subject matter.
Figure 1B:
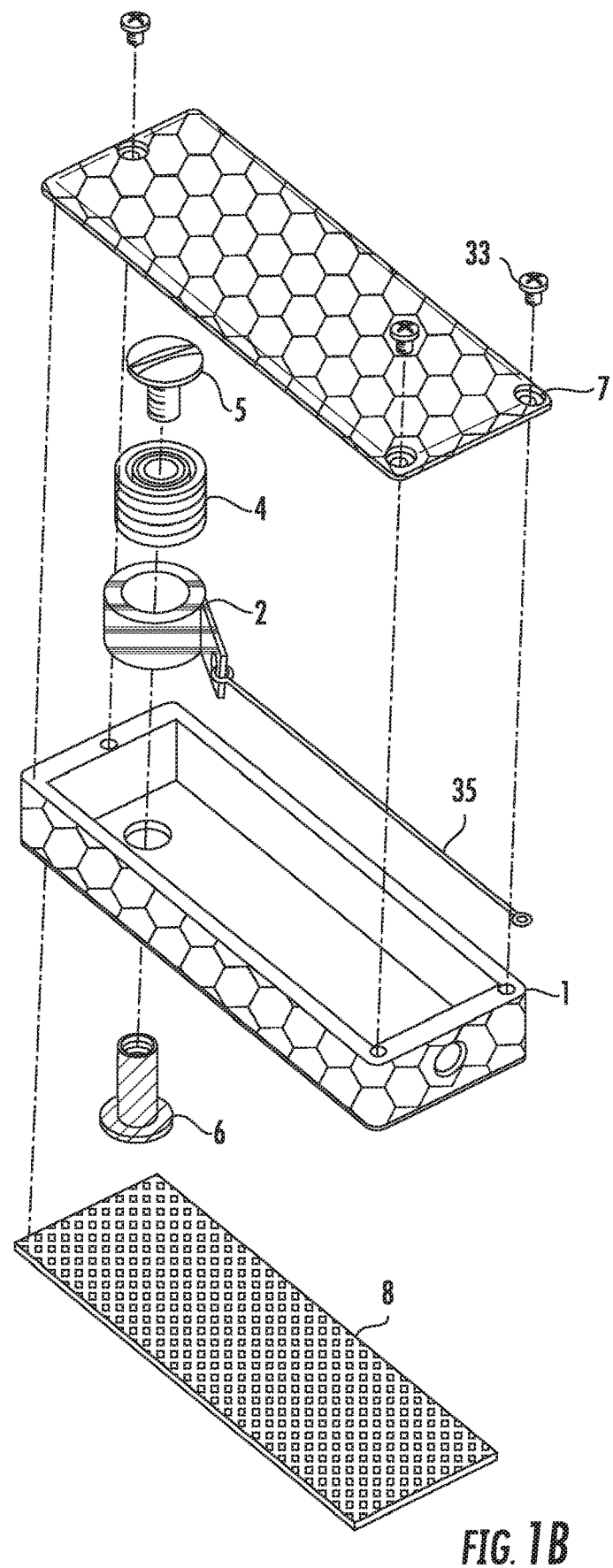
FIG. 1B is a partially exploded perspective view of the controlled tension device in which the spring rotates on a frictionless bearing shown in FIG. 1A. The controlled tension device can be secured to the brace shell with a strip of Velcro or a fastener.
Figure 1C:
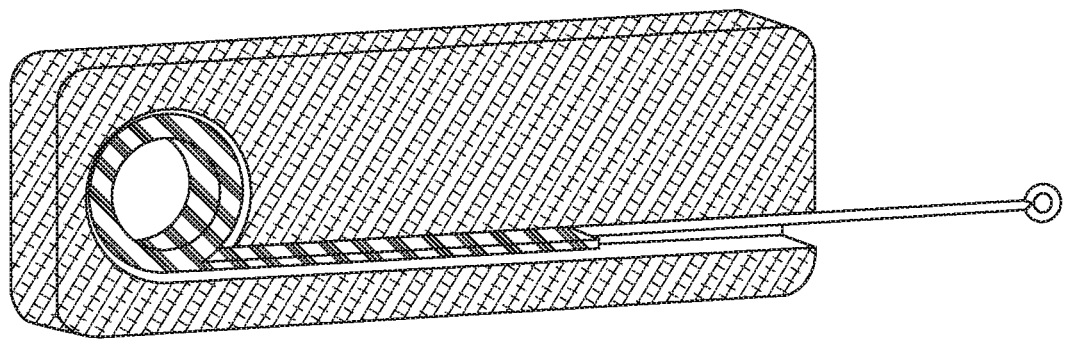
FIG. 1C is a perspective view of an alternate configuration of a controlled tension device according to an embodiment of the presently disclosed subject matter in which the constant force spring is contained in the housing using a cut-out section.

In this regard, the present subject matter provides controlled tension device fastening devices, systems, and methods. In one aspect, the presently disclosed subject matter provides a controlled tension fastening device that allows selective brace movement and represents an improvement in brace design towards a compliant (comfortable) brace that does not compromise the corrective force capacity of the brace. In the embodiment illustrated in FIGS. 1A through 1C, for example, a controlled tension unit, generally designated CTU, includes a housing or case 1 having an elongated shape. A constant-force spring 2 (e.g., a rolled ribbon of spring steel) is mounted within case 1. In some embodiments, constant-force spring 2 is mounted substantially at one end of case 1. A threaded bolt, rivet, or other fastener can be used to attach constant-force spring 2 to case 1. In the embodiments illustrated in FIGS. 1A and 1B, for example, a male rivet 5 and a female rivet 6 secure a bearing 4 (e.g., a "frictionless" bearing) within case 1, and constant-force spring 2 is coupled to bearing 4. A connector cable 35 is connected to the spring 2 and extends out of the case 1. In some embodiments, a lid 7 can be attached to case 1 (e.g., using lid screws 33), resulting in a closed system. In addition, in some embodiments, a Velcro strip 8 is provided on the back of case 1 and allows for quick attachment of controlled tension unit CTU to a preexisting Velcro strap on a brace. In the embodiment illustrated in FIG. 1C, case 1 is shown having a cut-out that locates the constant-force spring and has a defined length to establish a full rated load.

Constant-force springs have the capability of applying substantially the same force over a large range or working length within a load tolerance (e.g., to with 10% of the targeted value). In some embodiments, it is desirable to select a configuration for constant-force spring 2 such that an outside diameter of the bearing 4 is 15-20% greater than an inside diameter of constant-force spring 2, constant-force spring 2 has 1½ "wraps" remaining on the bearing when fully extended, and/or the full rated load is achieved when deflected a length of 1½ times bearing diameter. The tension setting of controlled tension unit CTU can be defined by the output force properties of constant-force spring 2. Therefore, different embodiments of controlled tension unit CTU can be made with various tension settings (e.g., typically between 10N and 100N) to allow for a wide range of tension selections. For example, different spring capacities for constant-force spring 2 can be selected (e.g., having representative force outputs of 20N, 30N, and 40N) to accommodate different strap tension settings.

Further in this regard, as discussed above, in some embodiments, case 1 has a length that is designed to allow a selected range of extension for constant-force spring 2 to thereby establish a full rated load of controlled tension unit CTU. In some particular embodiments, for example, the length of the housing is sufficient to accommodate a working range of between about 100% and 500% of an inner diameter of constant-force spring 2, including about 100%, 150%, 200%, 250%, 300%, 350%, 400%, 450% and 500%.

Figure 2A:
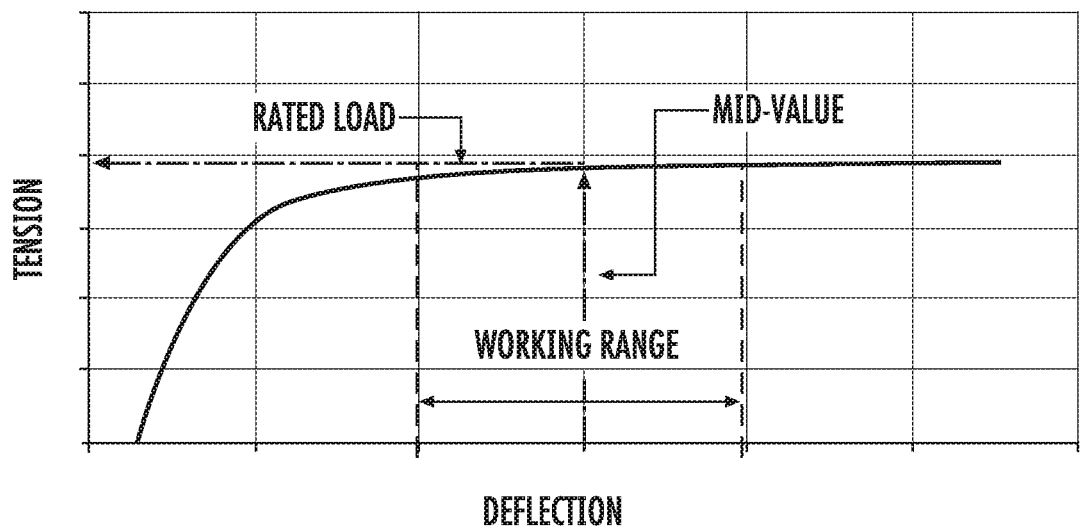
FIGS. 2A through 2D are graphs showing force-displacement behavior of a variety of constant-force springs for use with a controlled tension device according to an embodiment of the presently disclosed subject matter
Figure 2B:
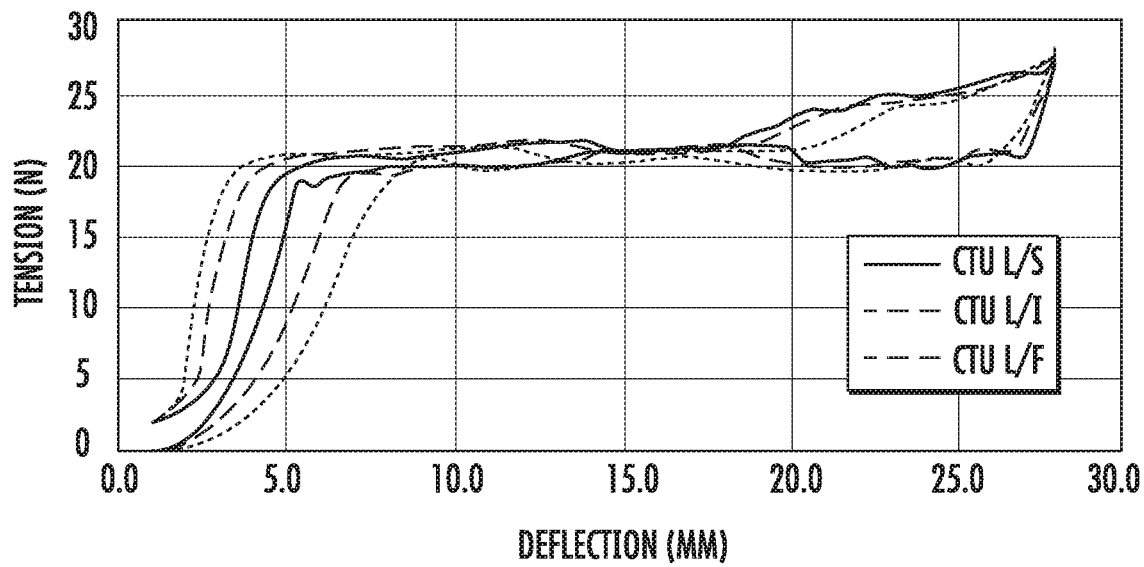
Figure 2C:
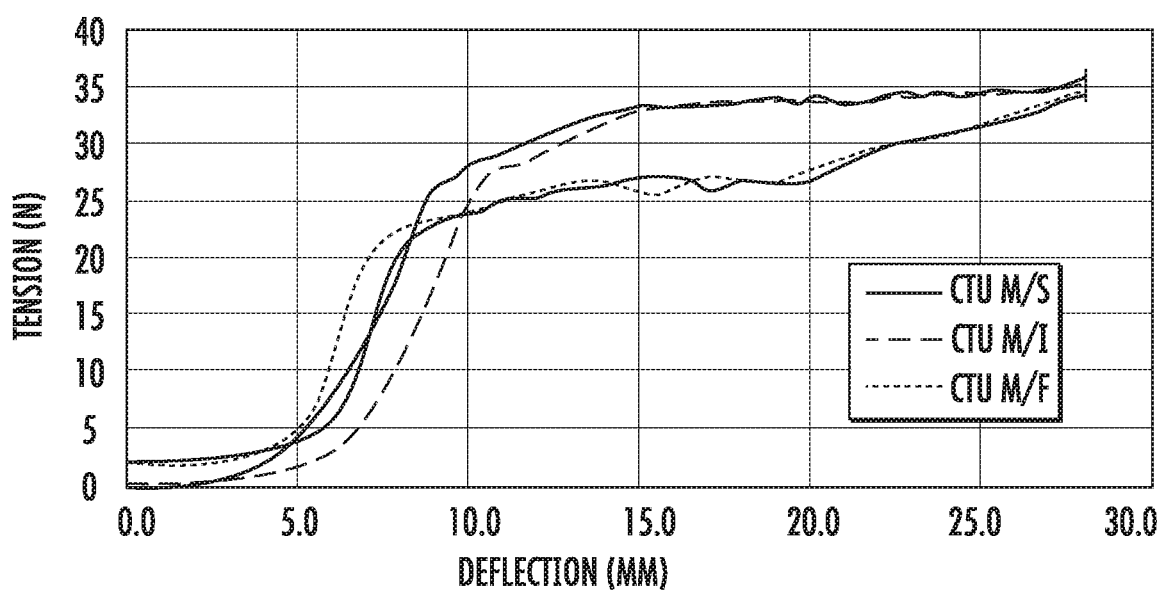
Figure 2D:
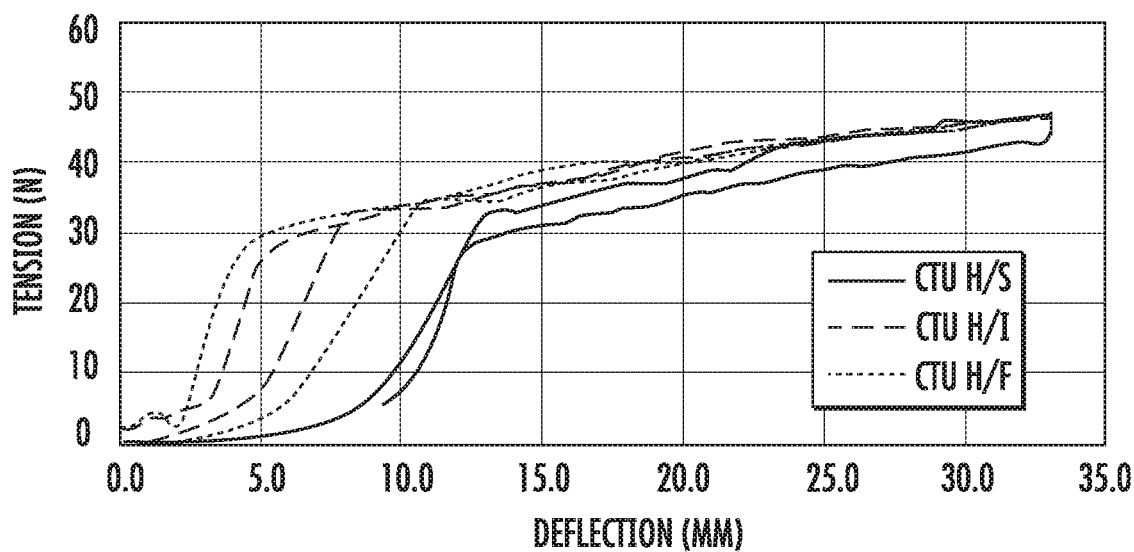

In some embodiments, constant-force spring 2 exhibits a force-displacement behavior as shown in FIGS. 2A through 2D. As illustrated in FIG. 2A, after some initial spring displacement, the change in the spring's force response is small over a large amount of spring displacement. Even when displaced at different speeds or rates, constant-force spring 2 still exhibits only a small change in tension over its working range as illustrated in FIGS. 2B through 2D. In particular, FIG. 2B illustrates the force-displacement behavior of a constant-force spring 2 having a "low" tension response (e.g., about 20N) at each of a fast speed (F) (e.g., maximum speed of about 18 mm/s), an intermediate speed (M) (e.g., maximum speed of about 12 mm/s), and a slow speed (S) (e.g., maximum speed of about 6 mm/s). Similarly, FIG. 2C illustrates the behavior of a constant-force spring 2 having a "medium" tension response (e.g., about 30N) at varying speeds, and FIG. 2C illustrates the behavior of a constant-force spring 2 having a "high" tension response (e.g., about 40N) at varying speeds. In each case, the targeted rated loads were substantially achieved and the load tolerances were all within a conventional spring manufacturer's specification of about 10%. The force output response and load tolerances can thus be substantially independent of the rate of spring displacement as shown in Table 1 below.

TABLE 1

Rated Load of controlled tension unit CTU

| Working Range Tension | Speed | | |
|---|---|---|---|
| | Slow | Intermediate | Fast |
| Low | Rated Load = 20.9N (4.7 lb) Load Tolerance = ±7% | Rated Load = 20.9N (4.7 lb) Load Tolerance = ±6% | Rated Load = 20.5N (4.6 lb) Load Tolerance = ±5% |
| Medium | Rated Load = 30.7N (6.9 lb) Load Tolerance = ±8% | Rated Load = 30.7N (6.9 lb) Load Tolerance = ±9% | Rated Load = 31.1N (7 lb) Load Tolerance = ±7% |
| High | Rated Load = 40N (9.0 lb) Load Tolerance = ±8% | Rated Load = 41.3N (9.3 lb) Load Tolerance = ±6% | Rated Load = 41.3N (9.3 lb) Load Tolerance = ±6% |

Figure 3:
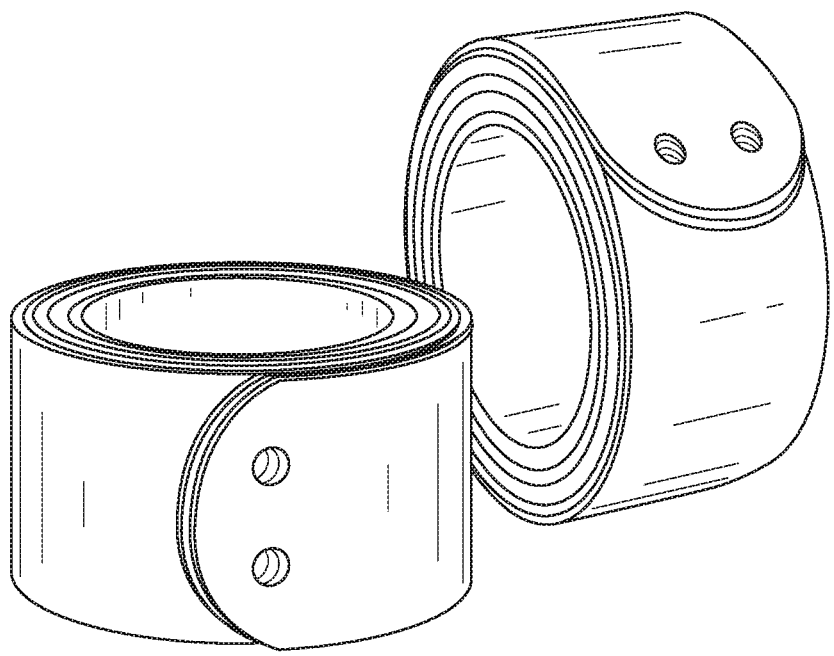
FIG. 3 is a perspective view of constant-force springs for use with a controlled tension device according to an embodiment of the presently disclosed subject matter.
Figure 4A:
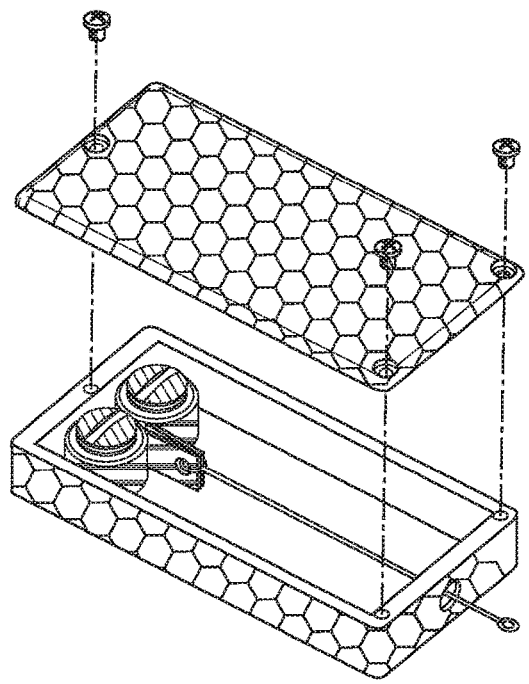
FIG. 4A is a partially exploded perspective view of a controlled tension device according to an embodiment of the presently disclosed subject matter.
Figure 4B:
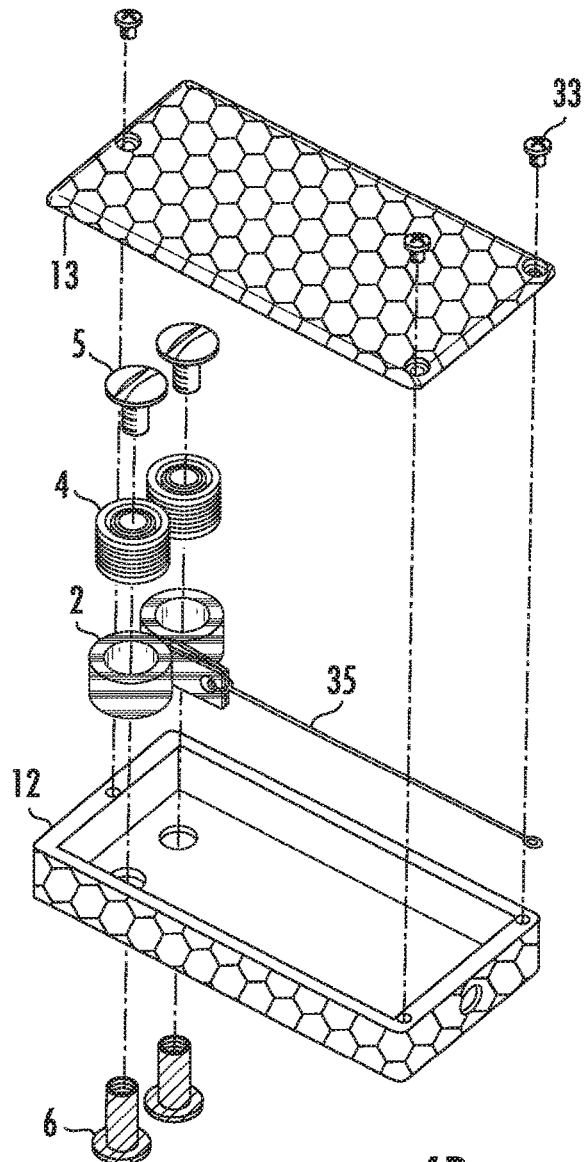
FIG. 4B is an exploded perspective view of the controlled tension device shown in FIG. 4A.

Constant force springs have a fatigue life that ranges from 2,500 cycles to over a million cycles. The force output of constant-force spring 2 is a function of the thickness, width, diameter, and material type. In some embodiments, for example, constant-force spring 2 is composed of stainless steel like most off-the-shelf constant force springs, although those having ordinary skill in the art will recognize that other material choices can be made to achieve the desired force response. Alternatively or in addition, in some embodiments, constant-force spring 2 comprises two or more constant-force springs that are laminated or otherwise stacked together (See, e.g., FIG. 3), whereby higher total forces can be achieved while maintaining a low profile design for controlled tension unit CTU. Furthermore, in some embodiments, a dual spring design using a large case 12 and a large lid 13 can be implemented to allow for further control over the tension settings of controlled tension unit CTU. (See, e.g., FIGS. 4A and 4B)

In any configuration, to connect constant-force spring 2 to another component to which tension is to be applied, a connector cable 35 is connected to an end of constant-force spring 2 and extends out of case 1, such as through an opening in a second end of case 1 (e.g., substantially opposing an end at or near which constant-force spring 2 is mounted). In this arrangement, when connector cable 35 is pulled, bearing 4 rotates about female rivet 6, and constant-force spring 2 is uncoiled. In this way, constant-force spring 2 can be extended towards the opposing end of case 1. An alternative case 1 has a cut-out space that locates the constant-force spring and has a defined length to establish a working load. The constant-force springs 2 are designed to work across a specific gap opening (e.g., the range of acceptable gap spacings for an associated brace) with a specified gap tolerance (e.g., ±6.3 mm (¼")). This tolerance is multiplied by a design factor (e.g., 3) to determine the working length (e.g., ±19 mm (¾")). The case 1 is designed with sufficient length to accommodate the working length of the constant-force spring 2 (e.g., 38 mm (1½")). Case 1 can further be designed to be low-profile so as to be worn comfortably under clothing and during daily activities. A lid 7 or 13 can be easily attached to case 1 (e.g., using lid screws 33), resulting in a closed system.

Regardless of the particular configuration, controlled tension unit CTU can be configured to be integrated into an orthotic bracing system to maintain a desired tension in the system. In some embodiments, for example, where the bracing system includes first and second portions separated by a gap, controlled tension unit CTU can be configured to maintain a preselected tension between the first portion and the second portion. In some embodiments, for example, the controlled tension unit CTU can be coupled to the first portion, and connector cable 35 can extend toward the second portion for coupling thereto.

Figure 5A:
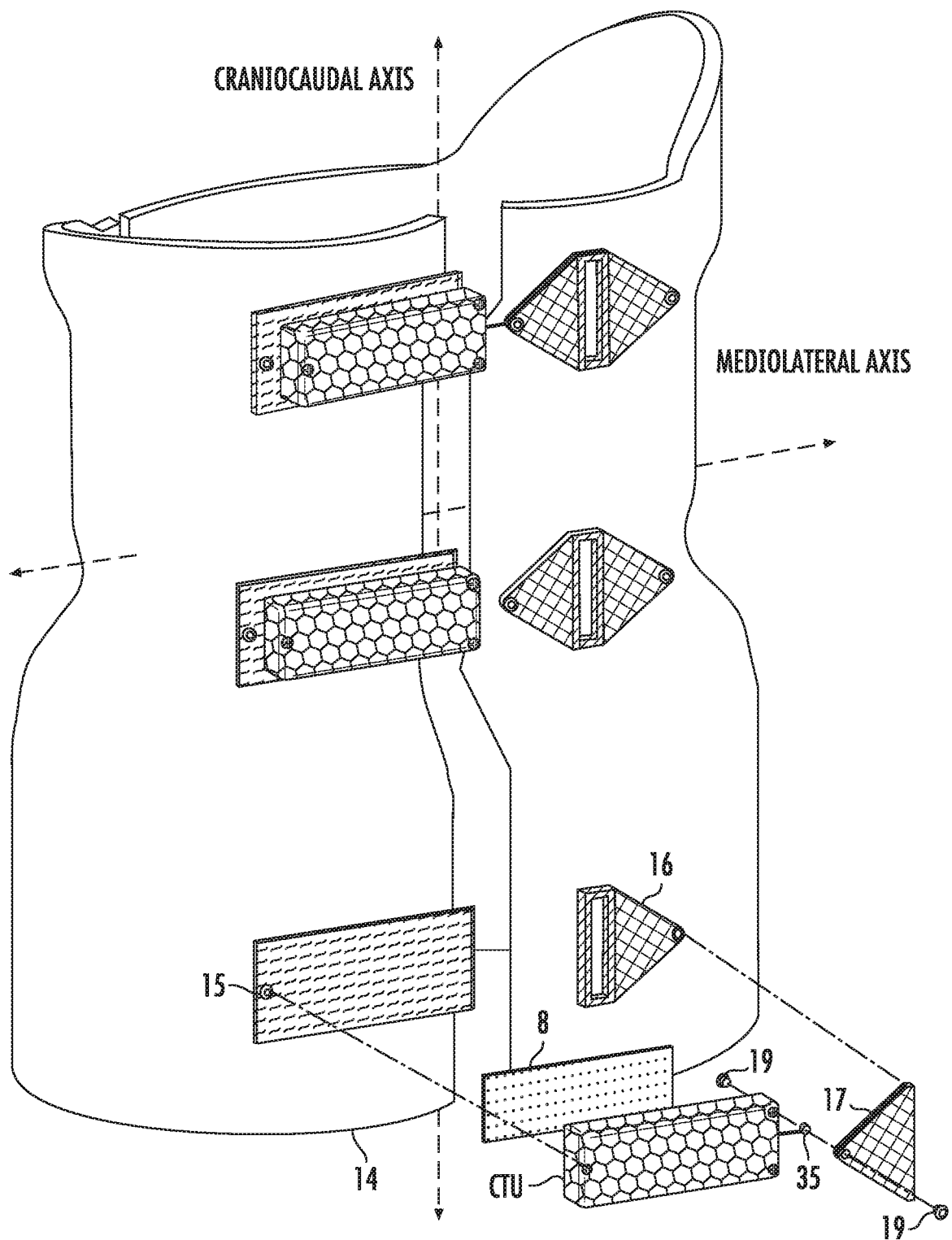
FIG. 5A is a perspective view of a scoliosis brace incorporating controlled tension devices according to an embodiment of the presently disclosed subject matter.

Referring to the embodiment illustrated in FIG. 5A, for example, the configuration of controlled tension unit CTU is designed to work with a type of strapping system currently used on a conventional scoliosis brace, generally designated 14. Referring to the configuration of brace 14 shown in FIG. 5A, in conventional systems, one or more Velcro strap 15 is designed to engage a complementary one or more strap (not shown) that can extend between portions of brace 14 and engage a corresponding chafe-and-loop arrangement 16 to secure the portions of brace 14 together as discussed above. For use with this configuration (e.g., as a retrofit for an existing brace), a Velcro strip 8 is provided on the back of case 1 and allows for quick attachment of controlled tension unit CTU to preexisting Velcro strap 15 on brace 14. In some embodiments, a chafe 17 connects the preexisting chafe-and-loop 16 on brace 14 to connector cable 35 (e.g., by compact rivets 19). In an alternative configuration for retrofit of an existing brace shown in FIG. 5B, controlled tension unit CTU is fixed to the back of the brace using fasteners (e.g., the same rivets 6 used to secure constant-force spring 2 within case 1) in place of the existing chafe and loop which are reattached to the connector cable 35 and allow for the preexisting Velcro strap 15 to secure portions of the brace.

Figures 6A, 6B:
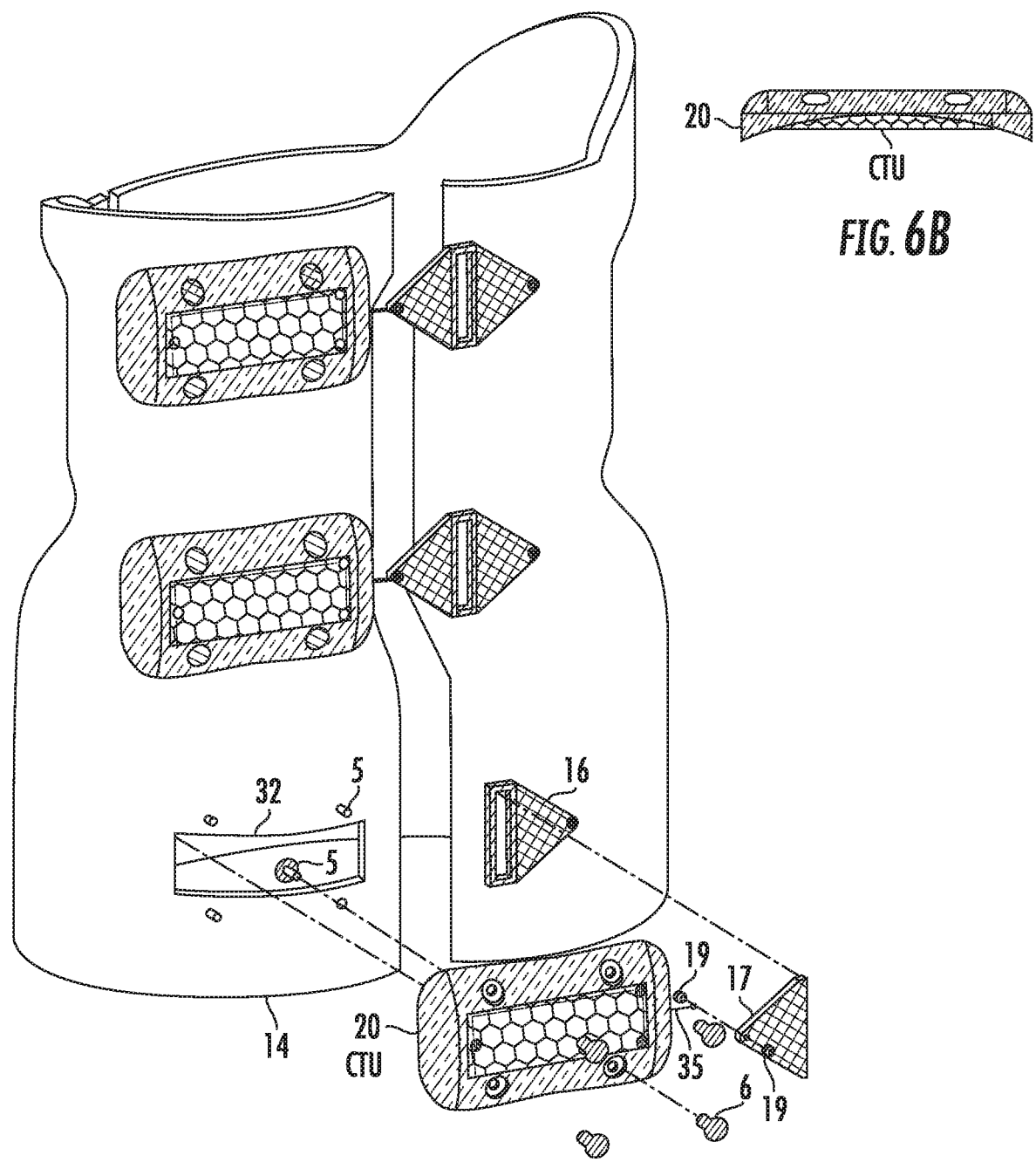
FIG. 6A is a perspective view of a scoliosis brace incorporating controlled tension devices according to an embodiment of the presently disclosed subject matter.
FIG. 6B is a side view of the controlled tension device incorporated into the scoliosis brace shown in FIG. 6A.
Figure 7:
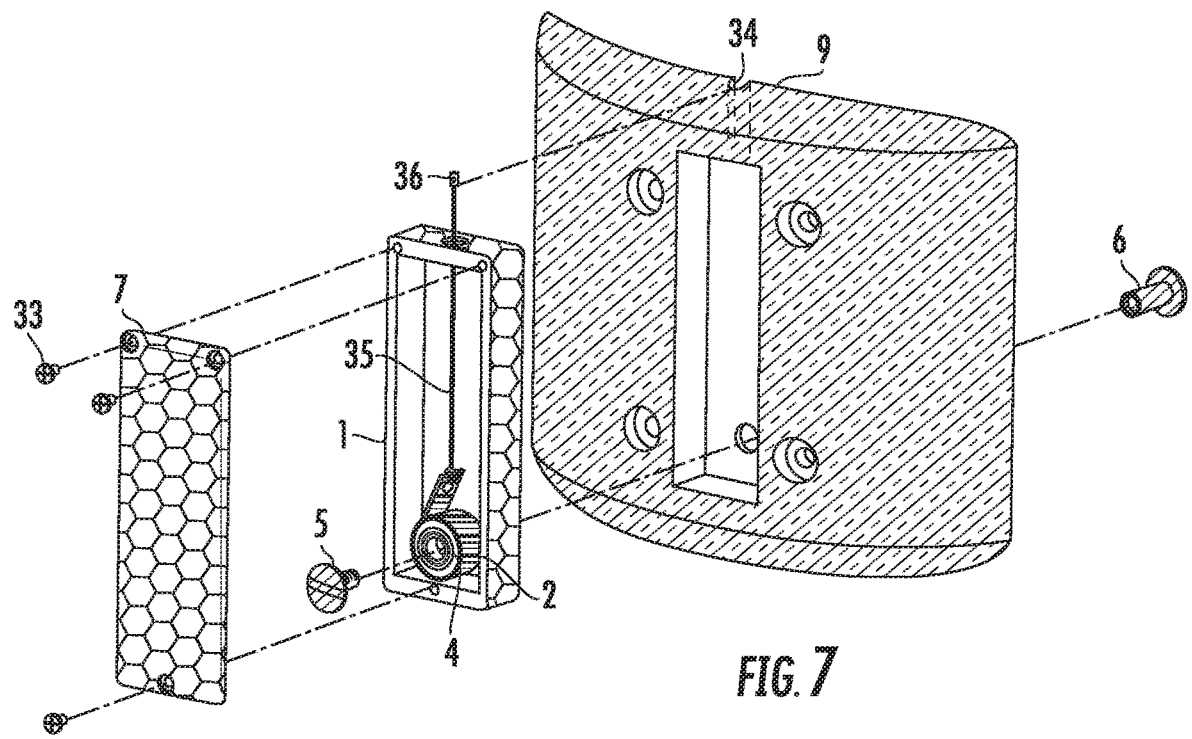
FIGS. 7 through 10 are exploded perspective views of various configurations for a controlled tension device according to embodiments of the presently disclosed subject matter.
Figure 8:
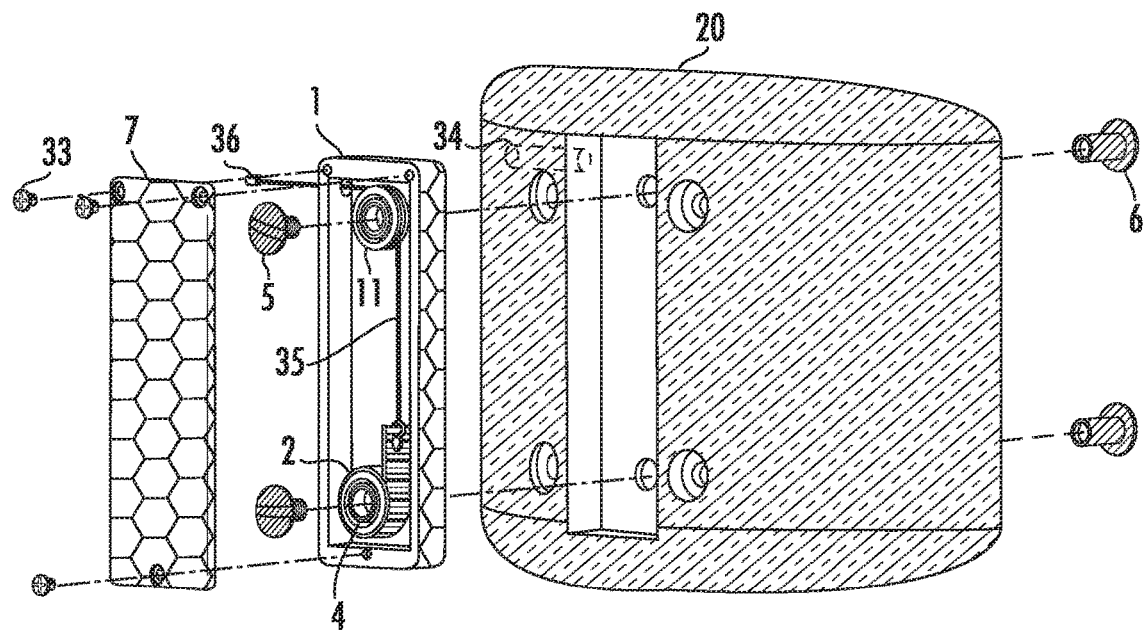
Figure 9:
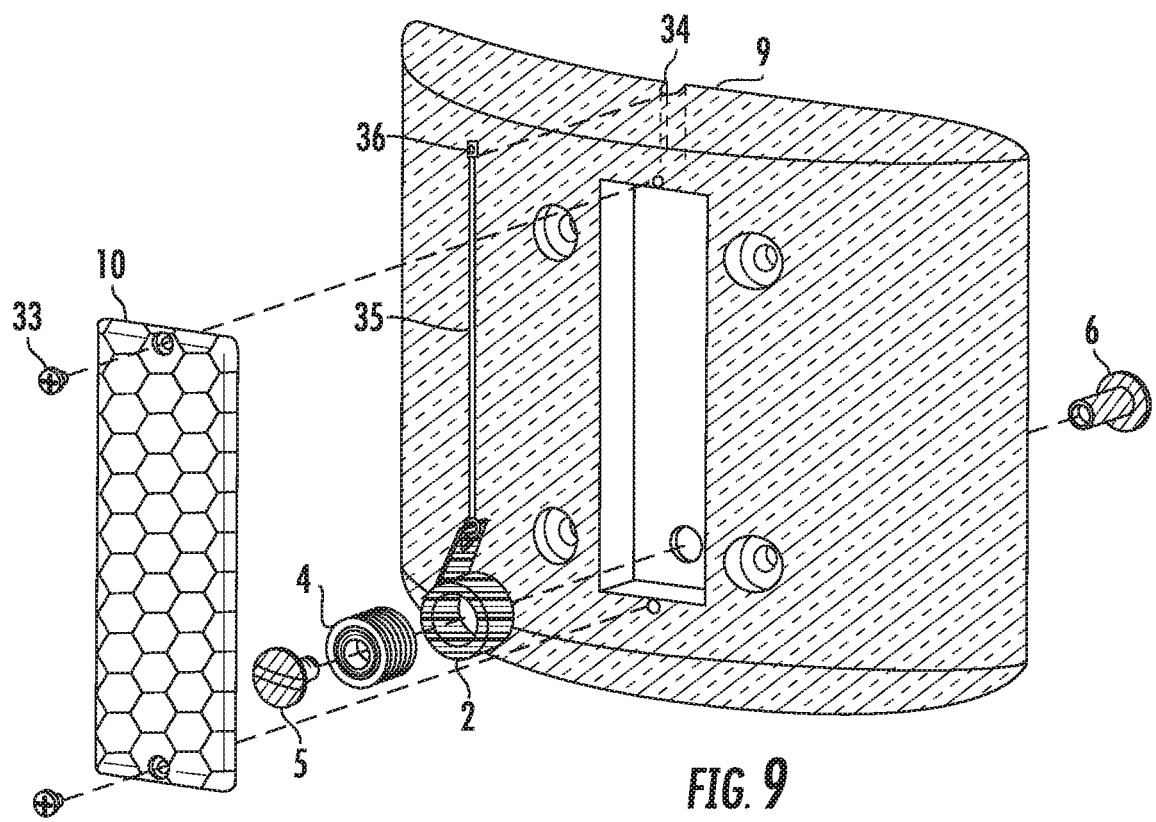
Figure 10:
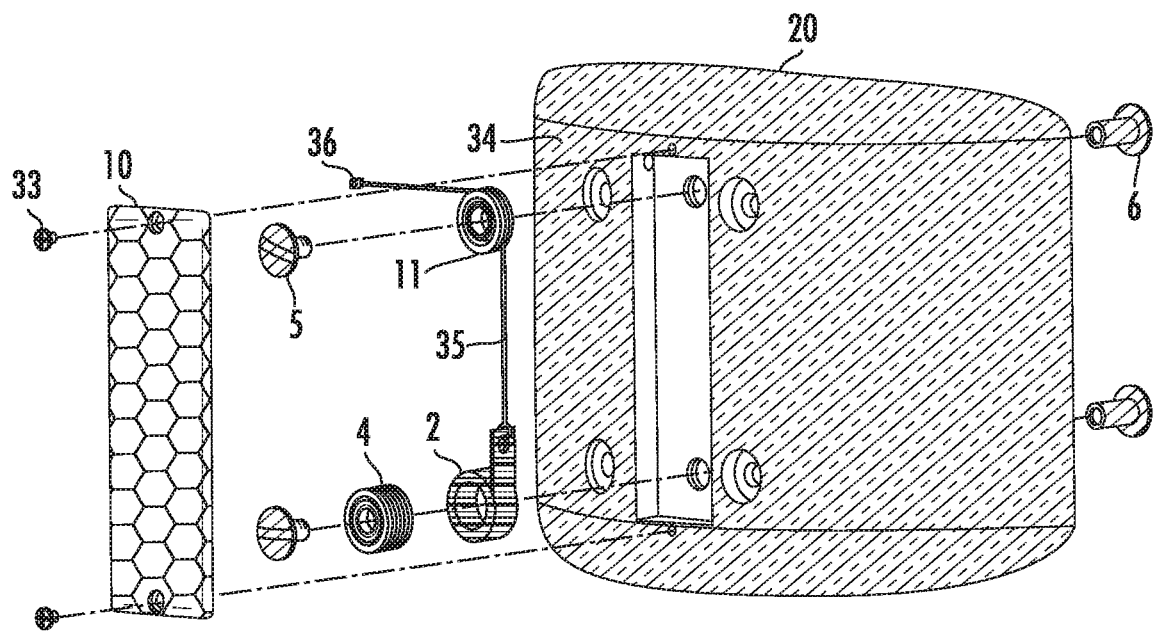

To allow for a lower profile design, FIGS. 6A and 6B show an embodiment of controlled tension unit CTU located inside a horizontal housing 20. The backside of controlled tension unit CTU keys into a slot 32 on brace 14. In some embodiments, housing 20 is riveted or otherwise fastened to brace 14. In other embodiments, controlled tension unit CTU is implemented in a vertical housing 9, such as is illustrated in FIG. 7. In some embodiments, connector cable 35 exits from vertical housing 9 through a cable slot 34 and has a cable connector 36 for easy attachment to an external cable. As illustrated in FIGS. 7 and 8, the positioning of cable slot 34 can be designed such that connector cable 35 exits out in any of a variety of positions, such as by providing cable slot 34 in either of a "vertical" (See, e.g., FIG. 7) or "horizontal" (See, e.g., FIG. 8) position. For configurations that use a horizontally-oriented arrangement for cable slot 34 out of housing 20, such as is shown in FIG. 8, a pulley 11 enables a turn (e.g., a right angle turn) of connector cable 35 before exiting through cable slot 34. In some embodiments in which pulley 11 is included to change a direction at which connector cable 35 extends away from constant-force spring 2, the length of case 1 can be further designed to be longer than that in a "vertical" configuration since the inclusion of pulley 11 can limit the extent to which constant-force spring 2 can be extended. FIGS. 9 and 10 show how the components can be imbedded directly into the housing.

Figure 11C:
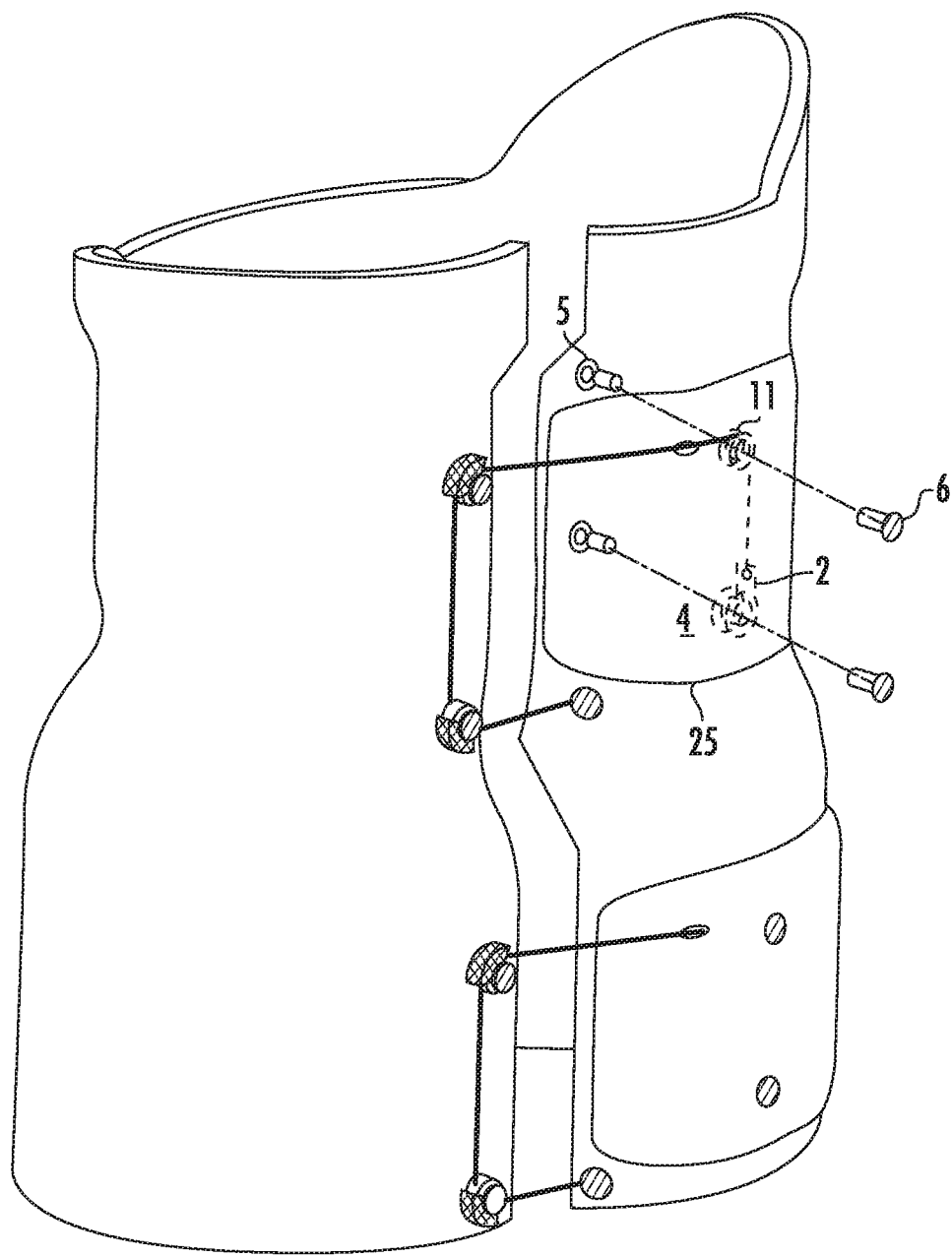
FIG. 11C is a perspective view of an alternate configuration in which a cavity in the shell of the brace is created such that a spring, frictionless bearings, and a pulley can be mounted from the inside of the brace using rivets and the cable spans a gap multiple times through the use of a pulley or system of pulleys.

Referring to FIGS. 11A and 11B, an example of how the aforementioned housings can be implemented into a brace is shown. In the illustrated embodiment, a vertical housing 9 with a horizontally-oriented arrangement for cable slot 34 is mounted to a brace. Connector cable is coupled to an external cable 3 (e.g., at cable connector 36), and external cable 3 is routed away from housing 9 (e.g., by an array of pulleys) and coupled to the brace at one or more positions selected to achieve the desired tension about brace. In some embodiments, pulley guards 22 prevent the cable from separating from the pulley. FIG. 11C shows how controlled tension unit CTU can be provided in a molded housing 25 formed in the brace itself.

Figure 11D:
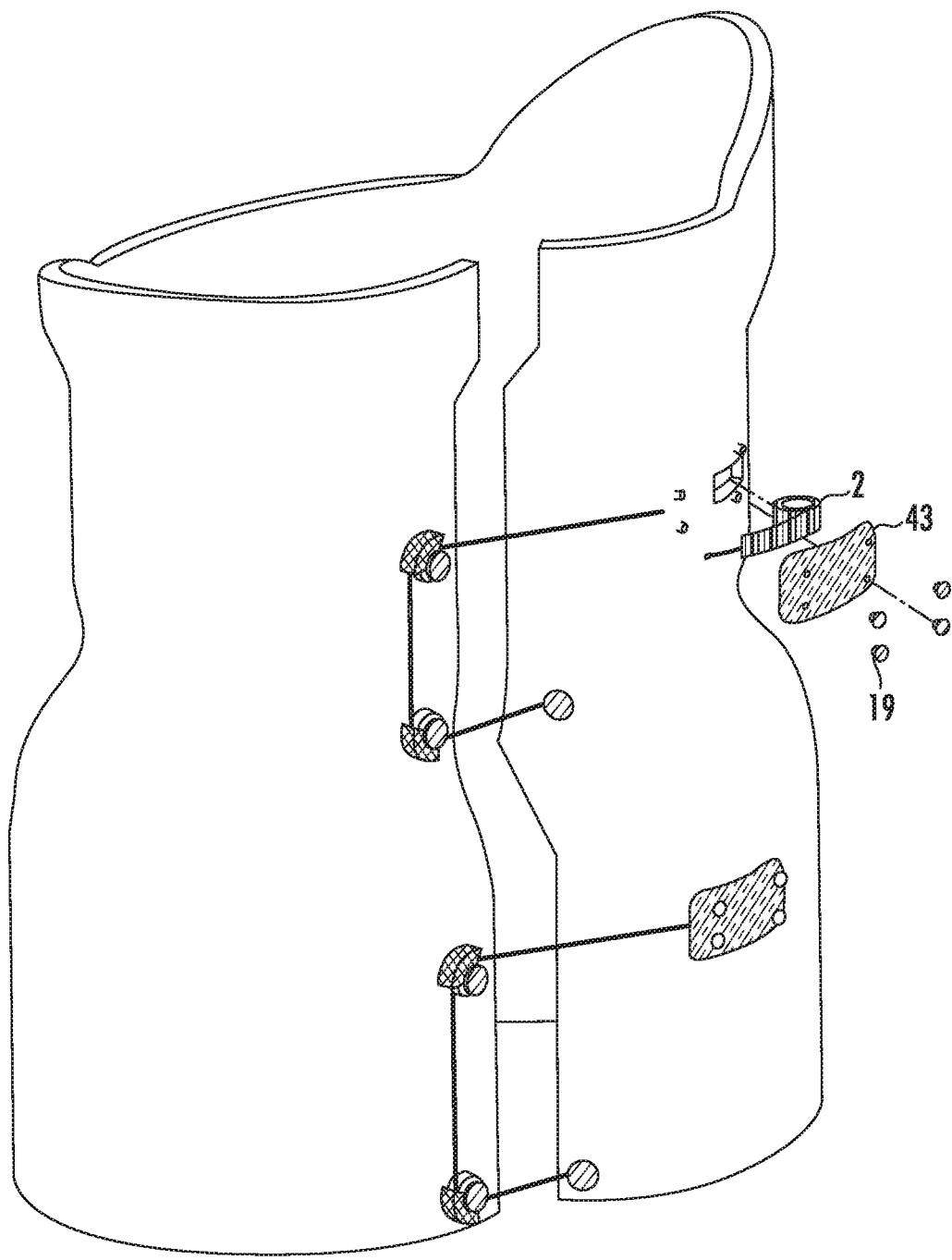
FIG. 11D is a perspective view of another alternate configuration in which a cavity in the brace allows a spring to sit flush against the outer shell of the brace as it unwinds and is held in place by a cover and the cable spans a gap multiple times through the use of a pulley or system of pulleys.

In yet a further alternative configuration shown in FIG. 11D, a cavity on the outside of the brace can accommodate constant force spring 2 so that the end of the spring sits flush against the outer shell of the brace as it unwinds. (See, e.g., FIG. 11D) In some embodiments, a cover plate 43 is positioned over the spring within a cavity to create a housing. In some such embodiments, cover plate 43 has a defined length selected to establish a full rated load. In this configuration, spring 2 sits flat against the outer surface of the brace and would be relatively low profile.

Regardless of what kind of attachment mechanism or device orientation is used for a given bracing system, the configurations of controlled tension unit CTU shown and described with respect to FIGS. 5 through 8 and 11A allow for a modular design of a bracing system in which controlled tension unit CTU can be easily interchanged with other units having different tension values.

Alternatively, in some embodiments, controlled tension unit CTU comprises a non-interchangeable design as shown in FIGS. 9, 10, 11C, and 11D. In these configurations, constant force spring 2 is directly mounted within vertical housing 9 (e.g., using bearing 4 and rivets 5 and 6) rather than in an intervening case 1. In some embodiments, this arrangement makes use of a housing lid 10 that directly attaches to vertical housing 9. For configurations in which cable slot 34 is oriented "horizontally" as shown in FIG. 10, a pulley 11 enables a right angle turn of connector cable 35 before exiting through cable slot 34. An alternative case 1 can have a cavity that locates the constant-force spring and has a defined length to establish a full rated load. In the further alternative housing configuration illustrated in FIG. 11D, constant force spring 2 is positioned within a cavity on the outside of the brace so that the end of the spring sits flush against the outer shell of the brace as it unwinds.

Figure 12A:
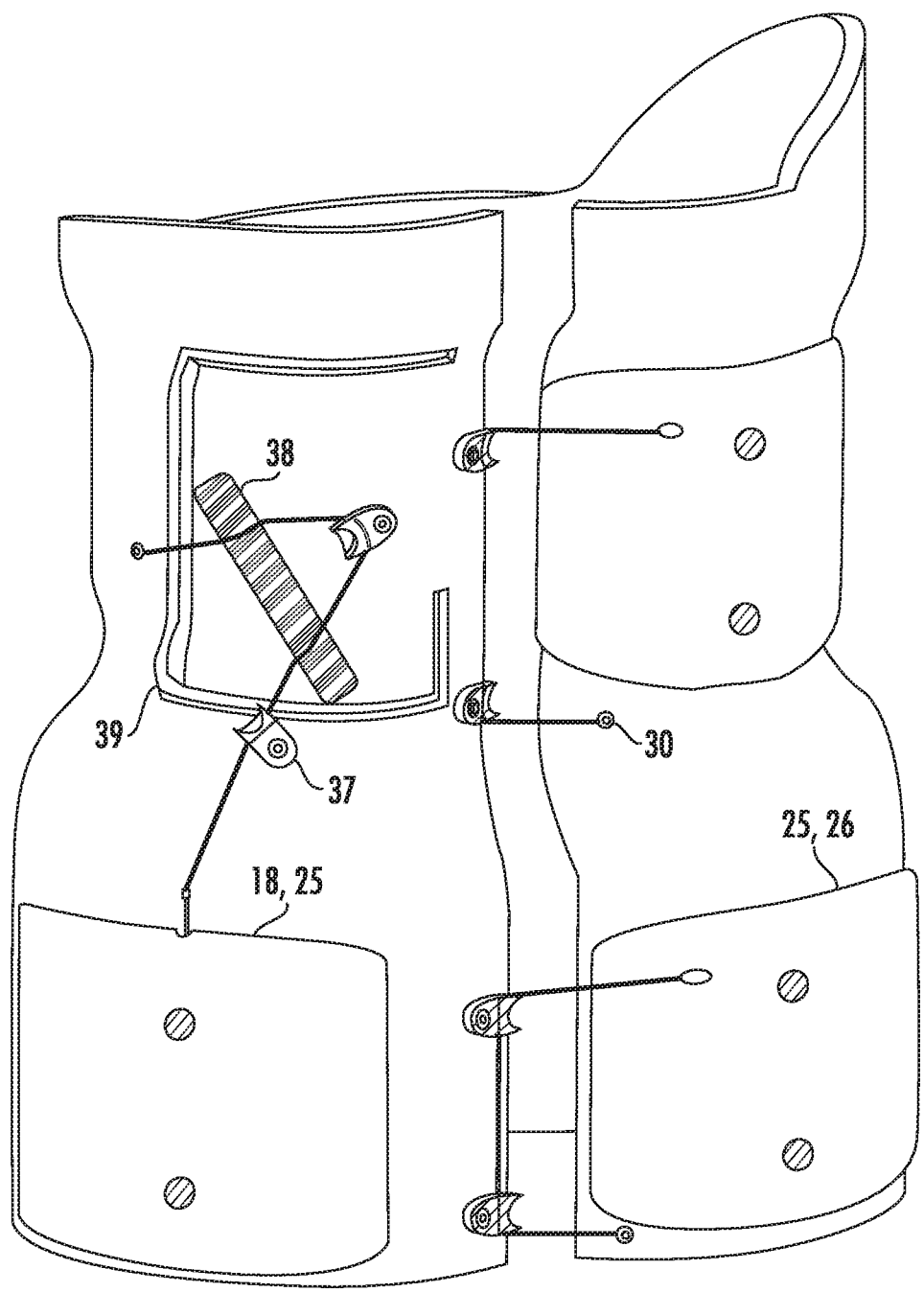
FIGS. 12A and 12B are perspective and side views of a dynamized scoliosis brace incorporating a riser located above a cantilevered cut-out flap around the apical brace pad. A pulley or system of pulleys is used to direct a cable over the riser that connects to a controlled tension device. Cable tension acts to displace the flap inward normal to the brace surface.
Figure 12B:
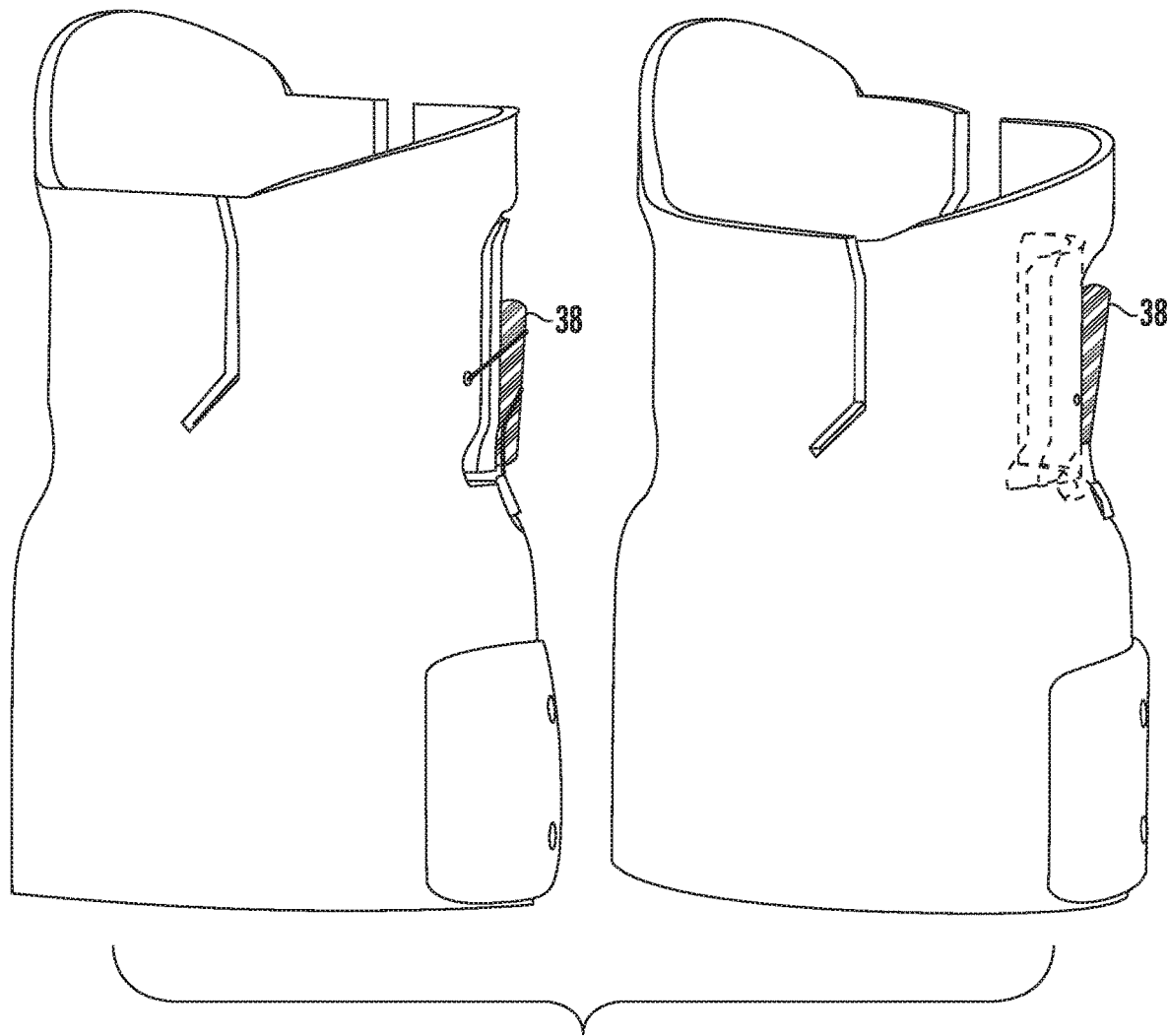

In all of these configurations, controlled tension unit CTU replaces conventional brace closures/straps for greater flexibility, improved comfort, and for maintaining strap tension. Alternatively or in addition, in some embodiments, controlled tension unit CTU 18 can be used to "dynamize" a standard brace (See, e.g., FIG. 12A). In this configuration, the design of the brace is modified to more effectively utilize the tension applied by controlled tension unit CTU. For example, in some embodiments, one or more strategic cut-out is provided in the brace, creating a movable portion of the brace (e.g., a cantilever flap 39) at a desired location (e.g., where the apical brace pad exists within the brace). The position of the movable portion can be displaced inward (e.g., normal to the brace surface) or outwards, such as by applying an input load across the movable portion via one or more controlled tension unit CTU. In this regard, in some embodiments, a cable riser 38 is strategically placed on a flap 39 to control the displacement of the flap and direct at least a portion of the cable load perpendicular to the cable axis. The cable extending from the controlled tension unit CTU is located using cable guides 37 and is fixed to the brace using an anchor rivet 30. The diameter or thickness of the riser 38 creates a gap between the cable and the brace surface such that when the cable is tensioned, the cantilever flap displaces inwards (See, e.g., FIG. 12B). In this way, the controlled tension unit dynamizes the loads applied by the apical brace pad to the torso.

Figure 12C:
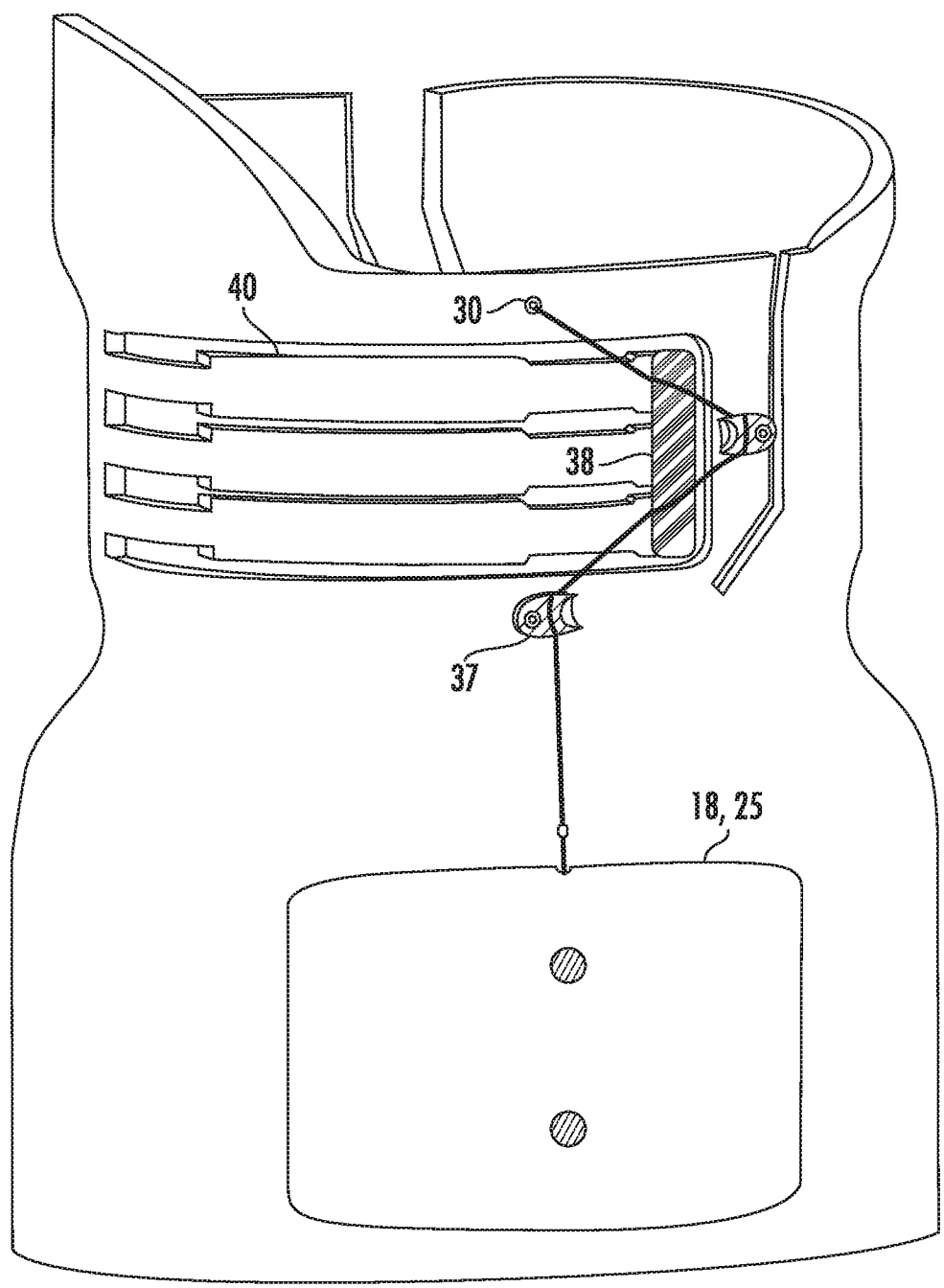
FIG. 12C and FIG. 12D are perspective and side views of a dynamized scoliosis brace with finger like cut-out sections located at the anterolateral side of the brace with a riser located above the fingers. A pulley or system of pulleys is used to direct a cable over the riser that connects to a controlled tension device. Cable tension acts to displace the fingers inward normal to the brace surface.
Figure 12D:
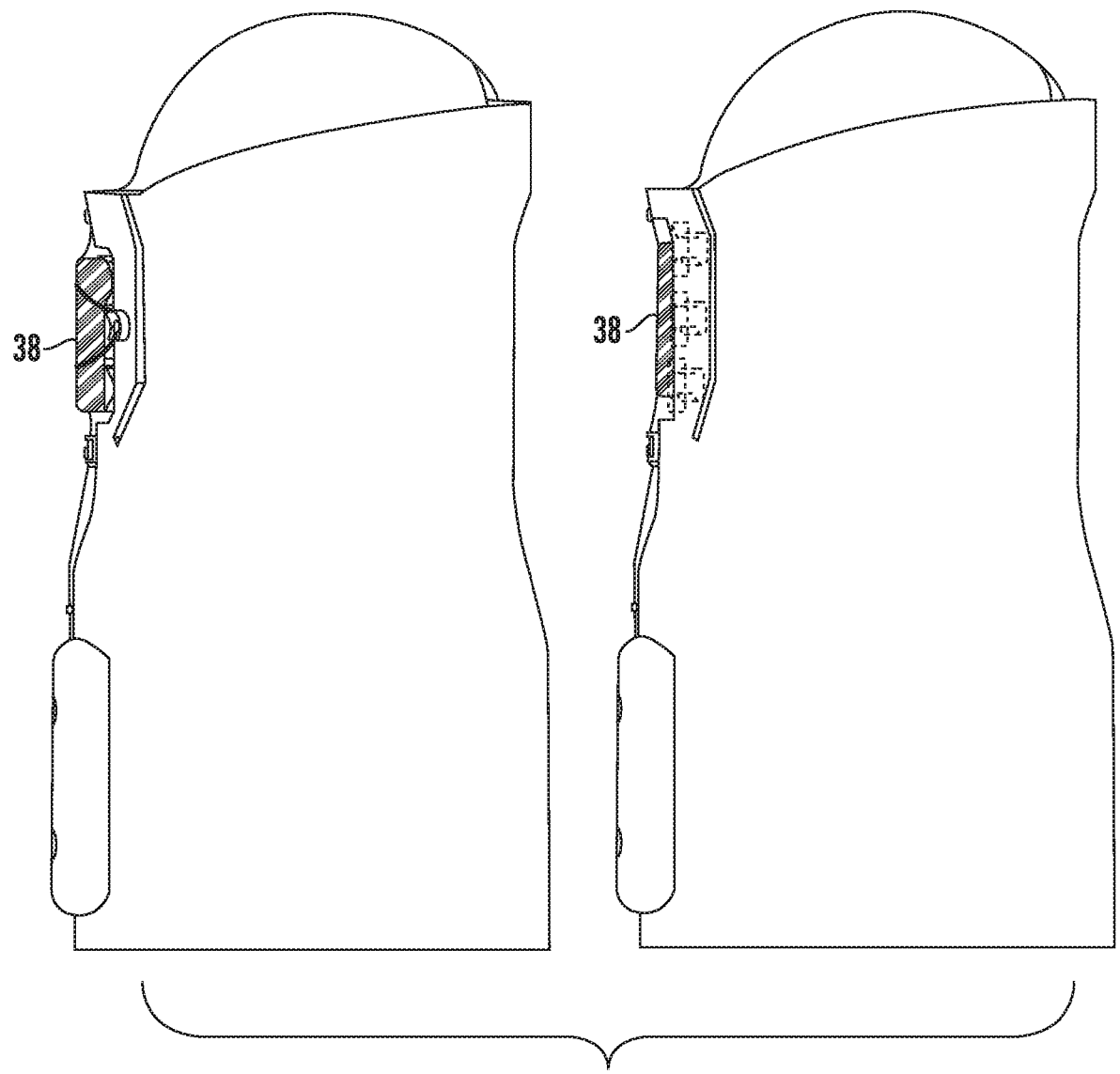
Figure 12E:
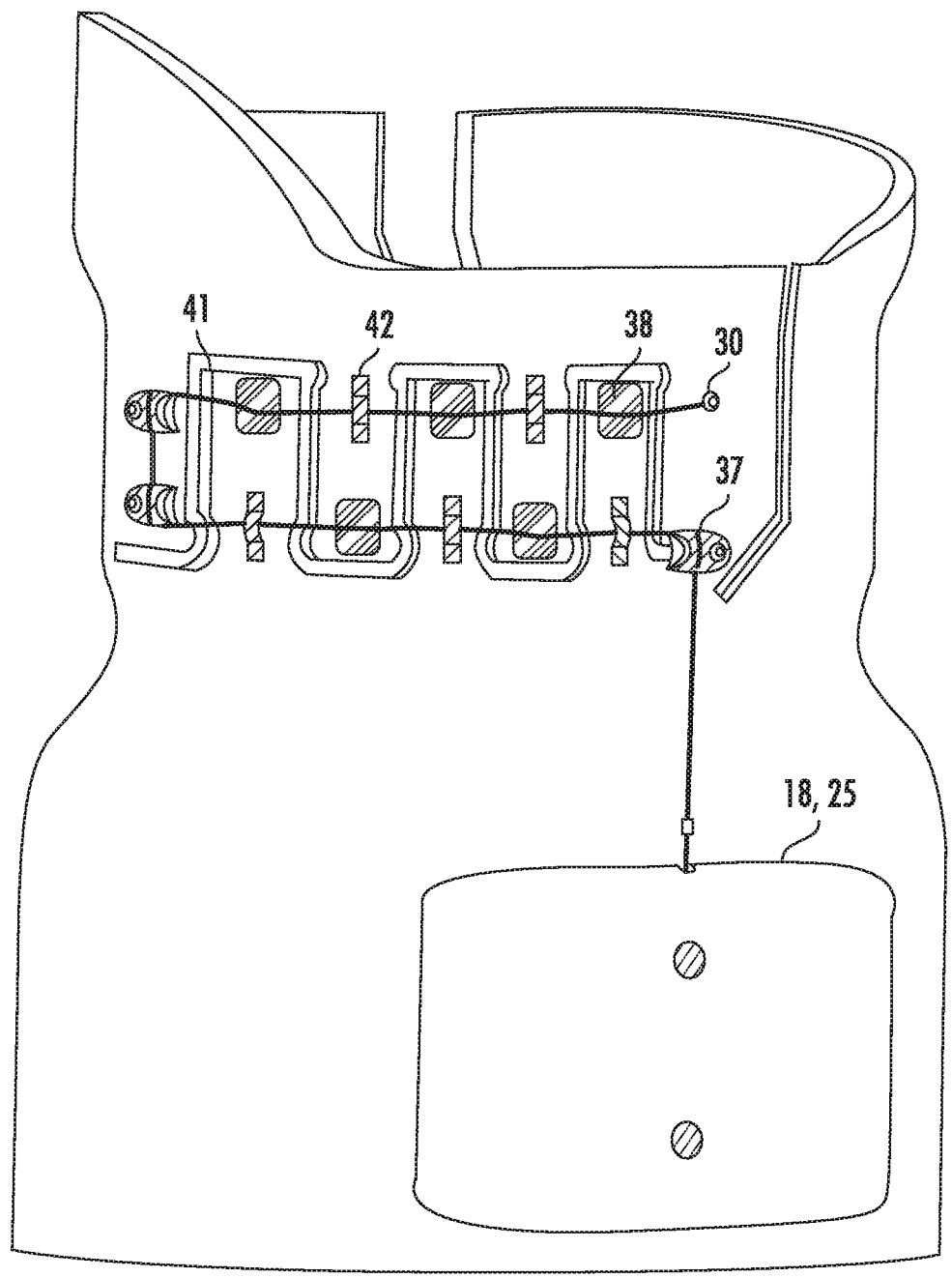

In another configuration (See, e.g., FIG. 12C), the cut-out has fingerlike geometry 40 with a horizontal orientation and is located around the anterolateral side of the brace. Controlled tension units CTU and risers 38 can be used to control the displacement and dynamic loading response of the individual fingers (See, e.g., FIG. 12D). Moreover, the stiffness of each individual finger can be controlled by altering the width of the base, which could result in improved comfort, flexibility, and/or curve correction. In another configuration (See, e.g., FIG. 12E), the cut-out has tab-like geometry 41 with a vertical orientation and located around the anterolateral side of the brace. These features provide a dynamic loading of the torso when used with a controlled tension unit CTU, risers 38, and cable guides 42 (See, e.g., FIG. 12F). However, due to the orientation of the interwoven tabs, the stiffness properties may be altered circumferentially which could result in improved comfort, flexibility, and/or curve correction.

Regardless of the particular configuration of controlled tension unit CTU, the associated brace can maintain the prescribed strap tension during a variety of typical daily living activities while still being more compliant and comfortable for the wearer. In particular, compared to conventional bracing systems, the incorporation of controlled tension unit CTU can result in a more compliant dynamic brace that allows for directional movement without compromising the corrective force capacity of the brace.

Figure 13A:
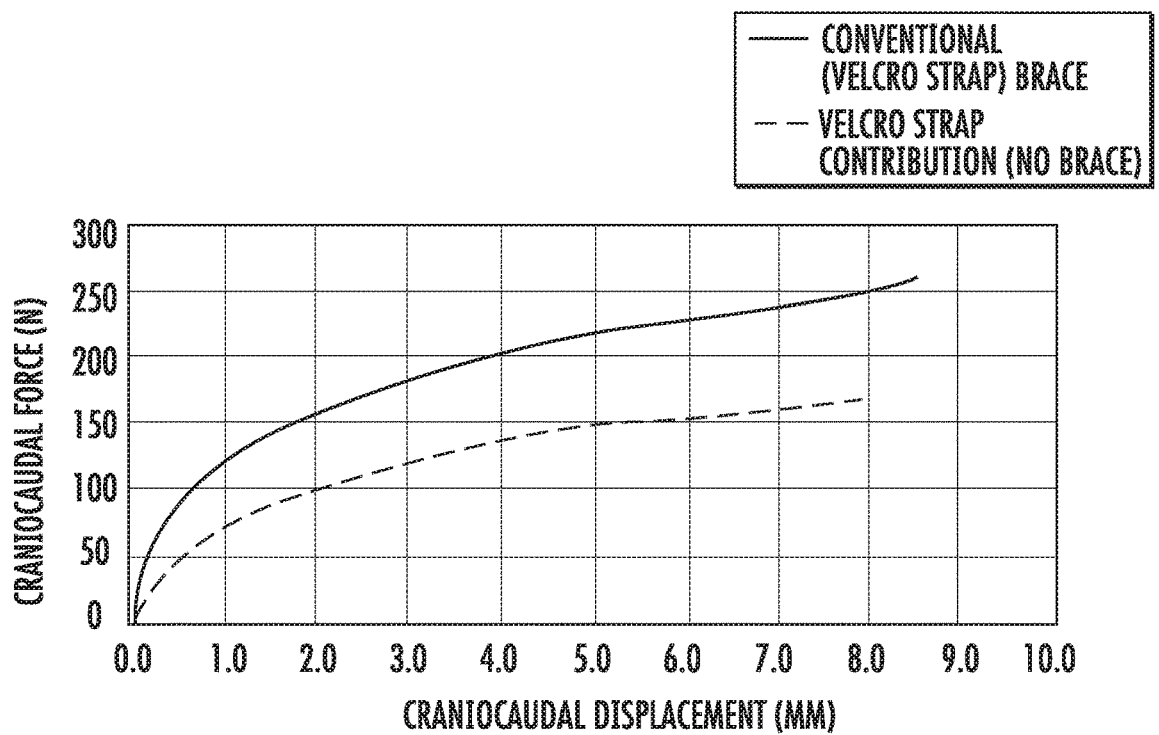
FIG. 13A is a graph illustrating reaction forces along the craniocaudal axis of the fastening devices relative to displacement in a conventional scoliosis brace with Velcro straps.
Figure 13B:
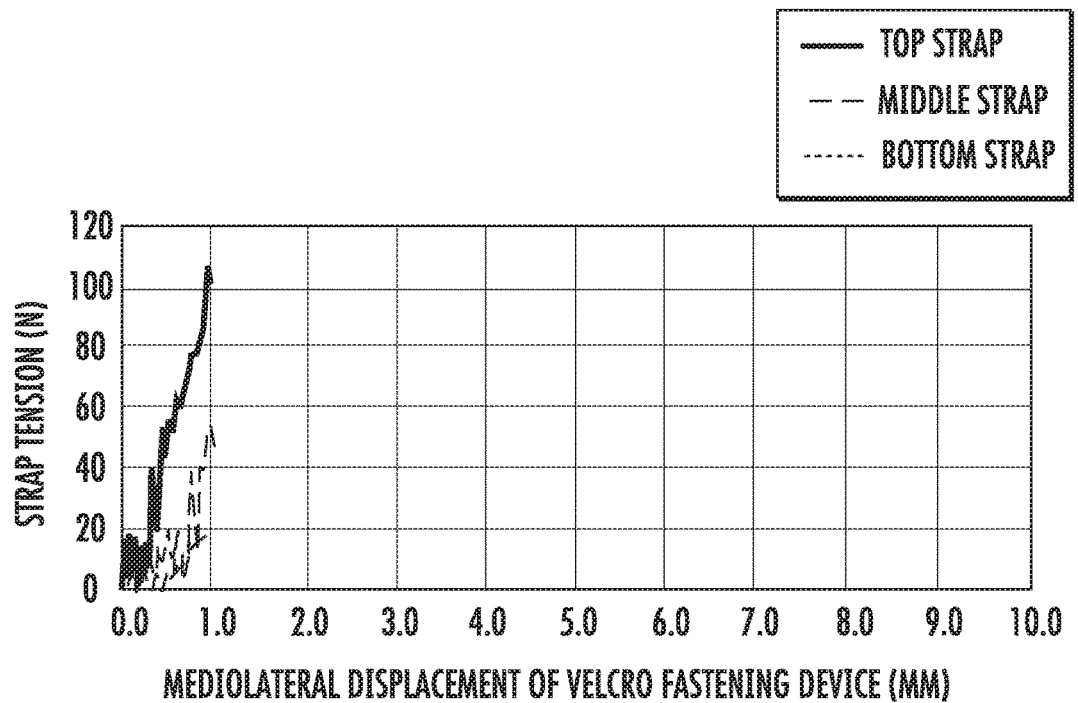
FIG. 13B is a graph illustrating strap tension along the mediolateral axis of the fastening devices relative to displacement in the conventional scoliosis brace with Velcro straps.

In this regard, comparative testing of different fastening systems can show that, for conventional configurations in which Velcro straps are used provide tension to a typical scoliosis brace (e.g., a "Boston" brace), only minimal displacement of the brace gap across which the straps are connected can be achieved. Furthermore, to the extent that small amounts of displacement can be achieved, both of the reaction forces in the craniocaudal axis (See, e.g., FIG. 13A) and the strap tension in the mediolateral axis (See, e.g., FIG. 13B) are highly correlated to the amount of displacement. In this way, very little range of movement is provided by the conventional configuration, and the little movement that can be achieved dramatically changes the corrective force applied by the brace.

Figure 14A:
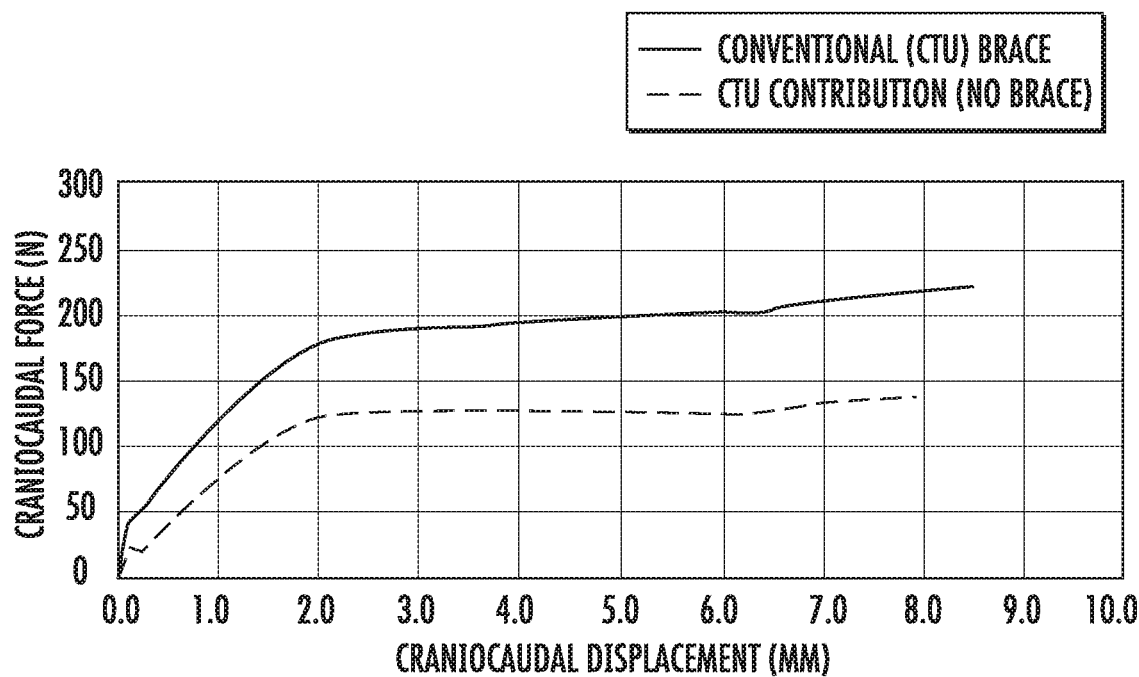
FIG. 14A is a graph illustrating reaction forces along the craniocaudal axis relative to displacement in a scoliosis brace incorporating controlled tension devices according to an embodiment of the presently disclosed subject matter.
Figure 14B:
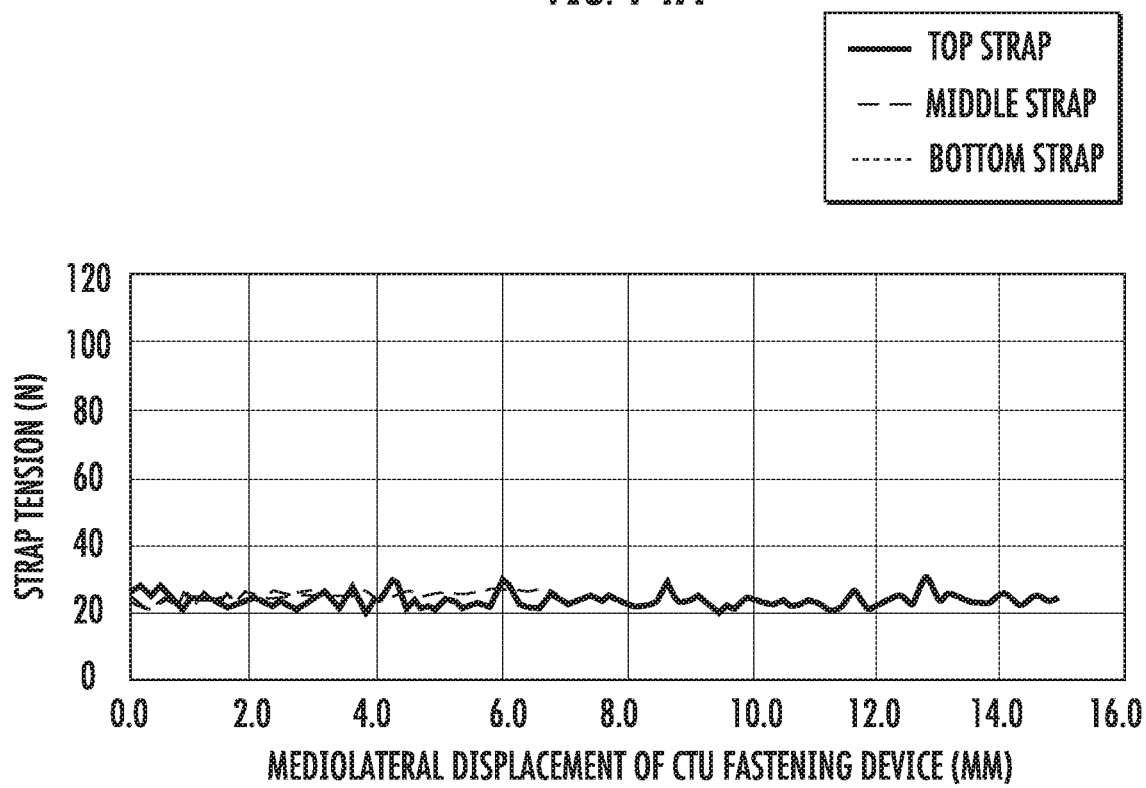
FIG. 14B is a graph illustrating strap tension along the mediolateral axis of the fastening devices relative to displacement in the scoliosis brace incorporating controlled tension devices according to an embodiment of the presently disclosed subject matter.

By comparison, in braces incorporating controlled-tension unit CTU, a greater range of brace-gap displacement is enabled compared to the Velcro straps. For these improved braces, the force-displacement behavior is substantially constant (see, e.g., graph of reaction forces in the craniocaudal axis shown in FIG. 14A). In fact, the force-displacement response (shown with a solid line) includes the contribution of the native brace itself, for which it is theorized that the inherent structural properties of the brace act like a conventional spring. The actual force-displacement properties of the CTU devices are shown with a dashed line, where the native brace contribution is subtracted from the overall response. In addition to providing substantially constant force-displacement behavior, the strap tension is likewise substantially constant over the range of displacement (See, e.g., graph of strap tension in the mediolateral axis shown in FIG. 14B) and can remain close to the tension value of the controlled-tension unit CTU used (e.g., approximately 20N). This evidence supports the design rationale that the strap tension setting will remain substantially independent of the brace gap, allowing for opportunities of deep breathing, increased range of movement, and/or improved brace force correction without a dramatic increase in resistive force or loss of corrective force.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

REFERENCES

1. Lou E, Hill D, Hedden D, Mahood J, Moreau M, Raso J. An objective measurement of brace usage for the treatment of adolescent idiopathic scoliosis. Med Eng Phys. April 2011; 33(3):290-294.
2. Aubin C E, Labelle H, Ruszkowski A, et al. Variability of strap tension in brace treatment for adolescent idiopathic scoliosis. Spine. Feb. 15, 1999; 24(4):349-354.
3. Pham V M, Houilliez A, Schill A, Carpentier A, Herbaux B, Thevenon A. Study of the pressures applied by a Cheneau brace for correction of adolescent idiopathic scoliosis. Prosthet Orthot Int. September 2008; 32(3):345-355.
4. Loukos I, Zachariou C, Nicolopoulos C, Korres D, Efstathopoulos N. Analysis of the corrective forces exerted by a dynamic derotation brace (DDB). Prosthet Orthot Int. December 2011; 35(4):365-372.
5. Wong M S, Evans J H. Biomechanical evaluation of the Milwaukee brace. Prosthet Orthot Int. April 1998; 22(1): 54-67.
6. Bateman C. Design, Validation, and Clinical Testing of Constant Tension Units and the Standard (CTU) Brace. Master's Thesis. UTHSC ET/D Library. 2016, pending publication.
7. Katz, D. E., Herring, J. A., Browne, R. H., Kelly, D. M., & Birch, J. G. (2010). Brace wear control of curve progression in adolescent idiopathic scoliosis. The Journal of Bone & Joint Surgery, 92(6), 1343-1352.
8. Wong, M. S., Cheng, J. C., Lam, T. P., Ng, B. K., Sin, S. W., Lee-Shum, S. L., . . . & Tam, S. Y. (2008). The effect of rigid versus flexible spinal orthosis on the clinical efficacy and acceptance of the patients with adolescent idiopathic scoliosis. Spine, 33(12), 1360-1365.
9. Zeh, A., Planert, M., Klima, S., Hein, W., & Wohlrab, D. (2008). The flexible Triac-Brace for conservative treatment of idiopathic scoliosis. An alternative treatment option. Acta Orthop Belg, 74(4), 512-521.

What is claimed is:

1. An orthotic brace comprising:
   a controlled tension unit coupled to a first portion of the orthotic brace, the controlled tension unit comprising:
   one or more constant-force spring; and
   a connector cable having a first end connected to an end of the one or more constant-force spring and a second end extending therefrom; and
   a coupling element coupled to a second portion of the orthotic brace, the coupling element being configured to couple with the second end of the connector cable, the second portion being separated from the first portion by a gap;
   wherein the controlled tension unit is configured to maintain a preselected tension between the first portion and the second portion of the orthotic brace;
   wherein one or both of the first portion or the second portion of the orthotic brace comprises one or more movable portions;
   wherein the controlled tension unit is configured to apply an input load across the movable portion to control a displacement of the movable portion.
2. The orthotic brace of claim 1, wherein the one or more constant-force spring is mounted to a housing that is integrally connected with the first portion of the orthotic brace.

3. The orthotic brace of claim 2, wherein the controlled tension unit comprises a fastener on a surface of the housing, the fastener being configured to couple to a complementary fastener on the first portion of the orthotic brace.

4. The orthotic brace of claim 2, wherein the housing has a length selected to accommodate the one or more constant-force spring with a desired total working range and has a defined length selected to establish a full rated load of the one or more constant-force spring.

5. The orthotic brace of claim 2, wherein the length of the housing is sufficient to accommodate a working range of between about 100% and 500% of an inner diameter of the constant-force spring.

6. The orthotic brace of claim 2, wherein each of the one or more constant-force spring is mounted to the housing about a bearing.

7. The orthotic brace of claim 2, wherein the one or more constant-force spring comprises two or more constant-force spring elements that are separately mounted to the housing.

8. The orthotic brace of claim 2, wherein the connector cable extends through a cable slot in communication between an interior and an exterior of the housing.

9. The orthotic brace of claim 8, wherein the one or more constant-force spring is mounted at or near a first end of the housing; and
wherein the cable slot is positioned in a wall of the housing at a second end of the housing substantially opposing the first end.

10. The orthotic brace of claim 1, wherein each of the one or more constant-force spring is mounted within a cavity.

11. The orthotic brace of claim 1, wherein the one or more constant-force spring comprises two or more constant-force spring elements that are laminated or otherwise stacked together.

12. The orthotic brace of claim 1, wherein the coupling element comprises a chafe-and-loop arrangement; and
wherein the controlled tension unit comprises a chafe connected to the second end of the connector cable, the chafe being configured to connect with the chafe-and-loop arrangement.

13. The orthotic brace of claim 1, comprising a pulley configured to change a direction at which the connector cable extends away from the one or more constant-force spring.

14. The orthotic brace of claim 1, wherein the connector cable is configured to span the gap multiple times through the use of a pulley or system of pulleys.

15. The orthotic brace of claim 1, wherein the controlled tension unit comprises a cable-riser configuration and the input load is in a direction normal to an axis of motion of the cable.

16. A controlled tension unit for an orthotic brace, the controlled tension unit comprising:
a housing;
one or more constant-force spring mounted to the housing; and
a connector cable having a first end connected to an end of the one or more constant-force spring and a second end extending out of the housing;
wherein the connector cable extends through a cable slot in communication between an interior and an exterior of the housing;
wherein the one or more constant-force spring is mounted at or near a first end of the housing; and
wherein the cable slot is positioned in a wall of the housing at a second end of the housing substantially opposing the first end.

17. The controlled tension unit of claim 16, wherein the housing has a length selected to accommodate the one or more constant-force spring with a desired total working range and has a defined length selected to establish a full rated load of the one or more constant-force spring.

18. The controlled tension unit of claim 16, wherein the length of the housing is sufficient to accommodate a working range of between about 100% and 500% of an inner diameter of the constant-force spring.

19. The controlled tension unit of claim 16, wherein each of the one or more constant-force spring is mounted to the housing about a bearing.

20. The controlled tension unit of claim 16, wherein each of the one or more constant-force spring is mounted within a cavity.

21. The controlled tension unit of claim 16, wherein the one or more constant-force spring comprises two or more constant-force spring elements that are laminated or otherwise stacked together.

22. The controlled tension unit of claim 16, wherein the one or more constant-force spring comprises two or more constant-force spring elements that are separately mounted to the housing.

23. The controlled tension unit of claim 16, comprising a chafe connected to the second end of the connector cable, the chafe being configured to connect with a chafe-and-loop arrangement on the orthotic brace.

24. A controlled tension unit for an orthotic brace, the controlled tension unit comprising:
a housing;
one or more constant-force spring mounted to the housing;
a connector cable having a first end connected to an end of the one or more constant-force spring and a second end extending out of the housing; and
a pulley mounted to the housing and configured to change a direction at which the connector cable extends away from the one or more constant-force spring;
wherein the connector cable extends through a cable slot in communication between an interior and an exterior of the housing.

25. A method for maintaining a preselected tension between a first portion and a second portion of an orthotic brace, the method comprising:
connecting a controlled tension unit to the first portion of the orthotic brace, the controlled tension unit comprising:
one or more constant-force spring; and
a connector cable having a first end connected to an end of the one or more constant-force spring and a second end extending therefrom; and
connecting a coupling element to the second portion of the orthotic brace; and
coupling the coupling element with the second end of the connector cable;
wherein one or both of the first portion or the second portion of the orthotic brace comprises one or more movable portions;
wherein connecting the coupling element with the second end of the connector cable comprises applying an input load across the movable portion to control a displacement of the movable portion.

* * * * *